(12) United States Patent
Clagett-Dame et al.

(10) Patent No.: US 7,528,114 B2
(45) Date of Patent: May 5, 2009

(54) C-LINKED GLUCURONIDE OF N-(4-HYDROXYBENZYL) RETINONE, ANALOGS THEREOF, AND METHOD OF USING THE SAME TO INHIBIT NEOPLASTIC CELL GROWTH

(75) Inventors: Margaret Clagett-Dame, Deerfield, WI (US); Robert W. Curley, Jr., Dublin, OH (US); Joel R. Walker, Tucson, AZ (US); Hussein Abou-Issa, Columbus, OH (US); Galal A. Alshafie, Columbus, OH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 142 days.

(21) Appl. No.: 11/416,907

(22) Filed: May 3, 2006

(65) Prior Publication Data
US 2006/0287255 A1 Dec. 21, 2006

Related U.S. Application Data

(60) Provisional application No. 60/677,503, filed on May 3, 2005.

(51) Int. Cl.
*C07H 1/00* (2006.01)
*A01N 43/04* (2006.01)
*C07C 49/00* (2006.01)
(52) U.S. Cl. ............... 514/23; 536/1.11; 568/329
(58) Field of Classification Search ............... None
See application file for complete search history.

(56) References Cited

U.S. PATENT DOCUMENTS 6,117,845 A * 9/2000 Clagett-Dame et al. ....... 514/35
2003/0171339 A1 * 9/2003 Sin et al. .................. 514/120

FOREIGN PATENT DOCUMENTS

WO    WO 94/11030 A      5/1994
WO    WO 2005092314 A1 * 10/2005

OTHER PUBLICATIONS

Abou-Issa, H.; Curley, R.W., JR.; Panigot, M. J.; Tanagho, S. N.; Sidhu, B. S.; Alshfie, G. A; Chemotheraputic Evaluation of N-(-Hydroxyphenyl) Retinamide-O-Glucuronide in the Rat Mammary Tumor Model;. *Anticancer Res.* 1997, 17, 3335.
Abou-Issa, H. M.; Alshafie, G. A.; Curley, R. W., Jr.; Wong, M. F.; Clagett-Dame, M.; Repa, J. J.; Sikri, V.; Chemopreventive Activity of a C-Glucuronide Analog of N-(4-hydroxyphenyl) Retinamide-O-Glucuronide Against Mammary Tumor Development and Growth; *Anticancer Res.* 1999, 19, 999.
Abou-Issa, H.; Curley, R.W., Jr.; Alshafie, G.A.; Weiss, K.L.; Clagett-Dame, M.; Chapman, J.S.; Mershon, S.M.; Chemotherapeutic Evaluation of 4-Hydroxybenzylretinone (4-HBR), a Nonhydrolyzable C-Linked Analog of N-(4-Hydroxyphenyl) Retinamide (4-HPR) against Mammary Carcinogenesis; *Anticancer Res.* 2001, 21, 3839.

Camerini, T., Mariani, L.; De Palo, G,; Marubini, E.; Gaetana Di Mauro, M.; Decensi, A.; Costa, A.; Veronesi, U.; Safety of the Synthetic Retinoid Fenretinide: Long-Term Results From a Controlled Clinical Trial for the Prevention of Contralateral Breast Cancer; *J. Clin Oncol.* 2001, 19, 1664.
Chapman, J. S.; Weiss, K. L.; Curley, R. W., Jr.; Highland, M. A.; Clagett-Dame, M.; Hydrolysis of 4-HPR to atRA occurs in vivo but is not required for retinamide-induced apoptosis; *Arch. Biochem. Biophys.* 2003, 419, 234.
Chomczynski, P.; Sacchi, N.; Single-Step Method of RNA Isolation by Acid Guanidinium Thiocyanate-Phenol-Chloroform Extraction; *Anal. Biochem.* 1987, 162, 156.
Clagett-Dame, M.; Repa, J.; Generating and Characterizing Retinoid Receptors from *Escherichia coli* and Insect Cell Expression System; *J. Meth. Enzymol.* 1997, 282, 13.
Costa, A.; Malone, W.; Perloff, M.; Buranelli, F.; Campa, T.; Dossena, G.; Magni, A.; Pizzichetta, M.; Andreoli, C.; Del Vecchio, M.; Formelli, F.; Barbieri, A.; Tolerability of the Synthetic Retinoid Fenretinide® (HPR); *Eur. J. Clin. Oncol.* 1989, 25, 805.
Curley, R.W., JR; Abou-Issa, H.; Panigot, M.J.; Repa, J.J.; Clagett-Dame, M.; Alshafie, G.; Chemopreventive Activites of C-Glucuronide/Glycoside Analogs of Retinoid-O-Glucuronides Against Breast Cancer Development and Growth; *Anticancer Res.* 1996, 16, 757.
Curley, R. W.; Carson, D.L; Synthesis of the 4-Oxygenated Retinoid Metabolites; *Drug Des. Delivery.* 1987, 1, 219-224.
Csuk, R.; Glaenzer, B. I.; Methylenation of Aldonolactones; *Tetrahedron* 1991, 47, 1655.
Davis, N. J.; Flitsch, S. L.; Selective Oxidation of Monosaccharide Derivatives to Uronic Acids; *Tetrahedron Lett.* 1993, 34, 1181.
Decensi, A.; Torrisi, R.; Gozza, A.; Severi, G.; Bertelli, G.; Fontana, V.; Pensa, F.; Carozzo, L.; Traverso, A.; Milone, S.; Dini, D.; Costa, A.; Effect of fenretinide on bone mineral density and metabolism in women with early breast cancer; *Breast Cancer Res. Treat.* 1999, 53, 145.

(Continued)

*Primary Examiner*—Shaojia Anna Jiang
*Assistant Examiner*—Layla Bland
(74) *Attorney, Agent, or Firm*—Joseph T. Leone, Esq.; DeWitt Ross & Stevens S.C.

(57) ABSTRACT

Compounds of the formula:

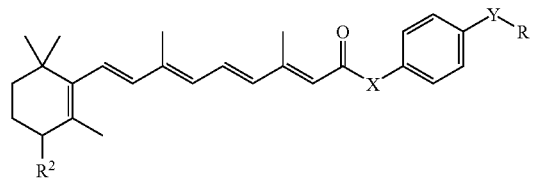

are described, along with pharmaceutical compositions containing these compounds, and methods of using the compounds to prevent and to treat cancer in mammals, including humans.

11 Claims, 5 Drawing Sheets

OTHER PUBLICATIONS

Dhem, A.; Goret-Nicaise, M.; *Effects of Retinoic Acid on Rat Bone*; Food Chem. Toxic. 1984, 22, 199.

Digiovanna, J. J.; Isotretinoin effects on bone; *J. Am. Acad. Dermatol.* 2001, 45, S176.

Formelli, F.; Carsana, R.; Costa, A.; Buranelli, F.; Campa, T.; Dossena, G.; Magni, A.; Pizzichetta, M.; Plasma Retinol Level Reduction by the Synthetic Retinoid Fenretinide: A One Year Follow-up Study of Breast Cancer Patients; *Cancer Res.* 1989, 49, 6149.

Formelli, F.; Clerici, M.; Campa, T.; Gaetana Di Mauro, M.; Magni, A.; Mascotti, G.; Moglia, D.; De Palo, G.; Costa, A.; Veronesi, U.; Five-Year Administration of Fenetinide: Pharmacokinetics and Effects on Plasma Retinol Concentrations; *J. Clin. Oncol.* 1993, 11, 2036.

Gerber, L. E.; Erdman, J. W. Jr.; Effect of retinoic acid and retinyl acetate feeding upon lipid metabolism in adrenlectomized rats; *J. Nutr.* 1979, 109, 580.

Gerber, L. E.; Erdman, J. W. JR.; Comparative effects of all-trans and 13-cis retinoic acid administration on serum and liver lipids in rats; *J. Nutr.* 1980, 110, 343.

Johns, B. A.; Pan, Y. T.; Elbein, A.D.; Johnson, C. R.; Synthesis and Biological Evaluation of Aza-Cdisaccharides: (1→6), (1→4), and (1→1); *J. Am. Chem. Soc.* 1997, 119, 4856.

Johnson, C. R.; Johns, B. A.; Susuki cross-coupling of carbohydrates; *Synlett* 1997, 1406.

Katz, H. E.; Chelate and Macrocycle Effects in the 2,2'-Bipyridine N,N'-Dioxide Complexation of Alkyltin Trichlorides; *J. Org. Chem.* 1985, 50, 2086.

Kelley, J. L.; Baker, B. R.; Irreversible Enzyme Inhibitors; J. Med. Chem. 1982, 25, 600.

Kobayashi, S.; Tsuchiya, Y.; Mukaiyama, T.; A Facile Synthesis of Cyanohydrin Trimethylsilyl Ethers by the Addition Reaction of Trimethylsyl Cyanide with Aldehydes under Basic Conditions; *Chem. Lett.* 1991, 4, 537.

Loerch, J. D.; Underwood, B. A.; Lewis, K. C.; Response of plasma levels of vitamin A to a dose of Vitamin A as an indicator of hepatic vitamin A reserves in rats; *J. Nutr.* 1979, 109, 778.

Loudig, l.; Babichuk, C.; White, J.; Abu-Abed, S.; Mueller, C.; Petkovich, M.; Cytochrome P450RA1(CYP26) Promoter: A Distinct Composite Retinoic Acid Response Element Underlies the Complex Regulation of Retinoic Metabolism; *Mol. Endocrinol.* 2000, 14, 1483.

Merrill, R.A.; Plum, L.A.; Kaiser, M.E.; Clagett-Dame, M.; A mammalian homolog of unc-53 is regulated by all trans retinoic acid in neuroblastoma cells and embryos; Proc. Natl. Acad. Sci. USA 2002, 99, 3422.

Modiano, M. R.; Dalton, W. S.; Lippman, S. M.; Joffe, L.; Booth, A. R.; Meyskens, F. L. Jr.; Phase II study of Fenretinide (N-[4-Hydroxyphenyl]retinamide)in advanced breast cancer and melanoma; *Invest. New Drugs* 1990, 8, 317.

Moon, R. C.; Metha, R. G.; Rao, K. V. N. Retinoids and cancer in expermental animals. In *The Retinoids Biology, Chemistry, and Medicine*, 2nd Edition; Sporn, M. B., Roberts, A. B., Goodman, D. S., Eds.; Raven Press: New York, 1994; p. 573.

Mulder, G. J.; Coughtrie, M. W. H.; Burchell, B. In *Conjugation Reactions in Drug Metabolism: An Integrated Approach*; Mulder, G. J., Ed.; Taylor and Francis: London, 1990; p. 52.

Panigot, M. J.; Humphries, K. A.; Curley, R. W., Jr.; Preparation of 4-retinoamidophynyl- and 4-retinamidobenzyl-c-glycosyl and c-glucuronosyl analogues of the glucuronide of 4-hydroxyphenyl=retinamide as potential stable cancer chemopreventive agents; *J. Carbohydr. Chem.* 1994, 13, 303.

Petasis, N. A.; Bzowej. E. I.; Titanium-Mediated Carbonyl Olefinations. 1. Methlenations of Carbonyl Compounds with Dimethyltitanocene; *J. Am. Chem. Soc.* 1990, 112, 6392.

Rajanbabu, T.V.; Reddy, G. S.; I-Methylene Sugars as C-Glycoside Precursors; *J. Org. Chem.* 1986, 51, 5458.

Robarge, M. J. Stable analogues of retinoid-O-glucuronides: Synthesis and biological activity. Dissertation, The Ohio State University, 1996.

Rohde, C. M.; Deluca, H.; Bone Resorption Activity of All-trans Retinoic Acid Is Independent of Vitamin D in Rats; J. Nutr. 2004, 133, 777.

Standevan, A. M.; Beard, R. L; Johnson, A. T.; Boehm, M. F.; Escobar, M.; Heyman, R. A.; Cheandraratna, R. A.; Retinoid-Induced Hypertriglyceridemia in Rats is Mediated by Retinoic Acid Receptors; *Fund. Appl. Toxicol.* 1996, 33, 264.

Stork, G.; Maldonado, L.; Anions of Protected Cyanohydrins as Acyl Carbanion Equivalents and Their Use in a new Synthesis of Ketones; *J. Am. Chem. Soc.* 1971, 93, 5286.

Veronesi, U.; De Palo, G.; Marubini, E.; Costa, A.; Formelli, F.; Mariani, L.; Decensi, A.; Camerini, T.; Rosselli Del Turco, M.; Di Mauro, M. G.; Muraca, M. G.; Del Vecchio, M.; Pinto, C.; D'aiuto, G.; Boni, C.; Campa, T.; Magni, A.; Miceli, R.; Perloff, M.; Malone, W. F.; Sporn, M. B.; Randomized Trial of Fenretinide to Prevent Second Breast Malignancy in Women with Early Breast Cancer; *J. Natl. Cancer Inst.* 1999, 91, 1847.

Walker, J. R.; Alshafie, G.; Abou-Issa, H.; Curley, R. W., Jr.; An Improved Synthesis of the C-Linked Glucuronide of N-(4-Hydroxyphenyl)retinamide; *Bioorg. Med. Chem. Lett.* 2002,12, 2447.

Weiss, K. L.; Alshafie, G; Chapman, J.S.; Mershon, S. M.; Abou-Issa, H.; Clagett-Dame, M.; Curley, R. W., Jr.; An Unhydrolyable Analogue of N-(4-Hydroxyphenyl)retinamide: Synthesis and Preliminary Biological Studies; *Bioorg. Med. Chem. Lett.* 2001, 11, 1583.

Weiss, K. L. Structural probes of retinoid action. Dissertation, The Ohio State University, 2001.

White, J.A.; Guo, Y.D.; Baetz, K.; Beckett-Jones, B.; Bonasoro, J.; Hsu, K. E.; Dilworth, F. J.; Jones, G.; Petkovich, M.; Identification of the Retinoic Acid-inducible All-trans-retinoic Acid 4-Hydroxylase; *J. Biol. Chem.* 1996, 271, 29922.

Wong, M. F.; Weiss, K. L.; Curley, R. W., JR.; Recent Improvements Towards the Synthesis of the C-Glucuronosyl Cancer Chemopreventive (β-D-Glucopyranosyluronate)-4-Retinamidophenylmethane; *J. Carbohydr. Chem.* 1996, 15, 763.

Wu. J.M.; Dipietrantonio, A.M.; Hsieh, T.-C.; Mechanism of fenretinide (4-HPR)-induced cell death; *Apoptosis* 2001, 6, 377.

Zanotti, G.; Berni, R.; Plasma Retinol-Binding Protein: Structure and Interactions with Retinol, Retinoids, and Transthyretin; *Vitam. Horm.* 2004, 69, 271.

Walker, et al., "Synthesis and preliminary chemotherapeutic evaluation of the fully C-linked glucuronide of N-(4-hydroxyphenyl) retinamide," *Bioorganic & Medical Chemistry*, Elsevier Science Ltd., GB, vol. 14, No. 9, pp. 3038-3048, 2006.

* cited by examiner

FIG. 3A
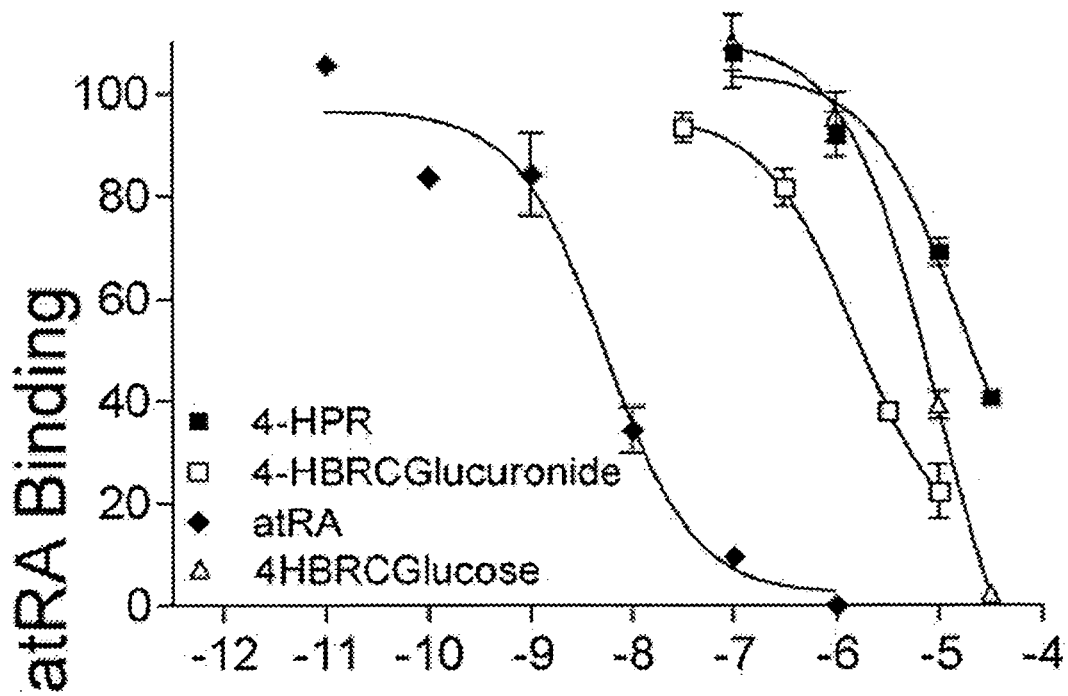
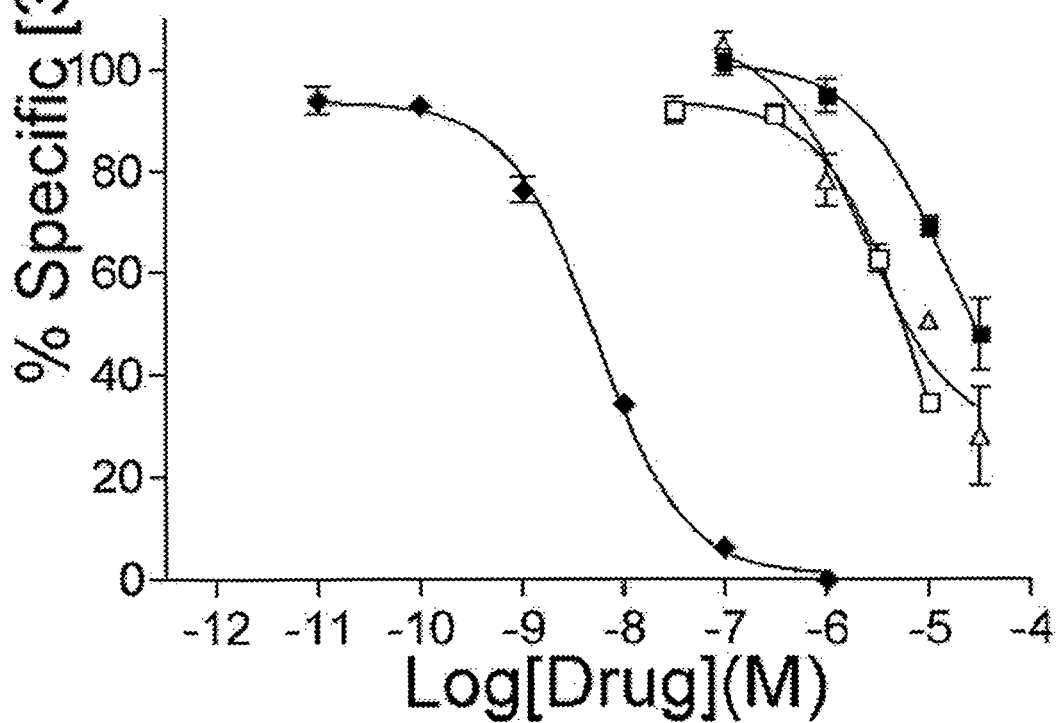
FIG. 3B

C-LINKED GLUCURONIDE OF N-(4-HYDROXYBENZYL) RETINONE, ANALOGS THEREOF, AND METHOD OF USING THE SAME TO INHIBIT NEOPLASTIC CELL GROWTH

CROSS-REFERENCE TO RELATED APPLICATIONS

Priority is hereby claimed to provisional application Ser. No. 60/677,503, filed May 3, 2005, which is incorporated herein.

FEDERAL FUNDING STATEMENT

This invention was made with United States government support awarded by the following agency: NIH CA049837. The United States government has certain rights in this invention.

INCORPORATION BY REFERENCE

All of the references cited below are incorporated herein.

BACKGROUND

Retinol (compound 1) and its metabolites are involved in regulating many biological processes including vision, cell differentiation, and growth. Besides being essential to normal cell function, the retinol metabolite all-trans retinoic acid (RA, 2) also shows antiproliferative action in cancer.[1] At pharmacologically effective doses, however, RA causes severe toxicity. Therefore, development of retinoid analogs possessing a higher therapeutic index is needed. One of the most investigated synthetic retinoids is N-(4-hydroxyphenyl) retinamide (4-HPR; compound 3), which has been shown to be effective in numerous types of animal tumor models and has been evaluated in a phase III clinical trial.[2] A possible benefit was reported for the prevention of second breast malignancy in premenopausal women with surgically removed stage I breast cancer or ductal carcinoma in situ. Although 4-HPR is generally well tolerated, it results in a decrease in plasma retinol levels[3,4] and concomitant diminished dark adaptation. Dermatological disorders were reported in a substantial number of subjects.[5]

Glucuronidation of drugs and natural products is a common metabolic pathway that usually facilitates excretion.[6] An important metabolite of 3 is 4-HPR-O-glucuronide (4-HPROG; compound 5) in which the phenolic hydroxyl group is linked to the sugar. Subsequent to its discovery, compound 5 was synthesized and evaluated for bioactivity, and was shown to have excellent chemopreventative activity in a rat mammary tumor model.[7] However, it was not determined if the glucuronide 5, which was shown to be hydrolyzed to compound 3 via β-glucuronidase,[8] was advantageous due to improved bioavailability of 3 or had activity in its own right as intact 5. To study this issue, an enzymatically stable glucuronide analog was synthesized by replacing the phenolic oxygen with a methylene group. The carbon-linked analog 4-HPR-C-glucuronide (4-HPRCG; compound 6) was shown to have excellent chemopreventative[9] and chemotherapeutic[10] properties. Furthermore, much like 4-HPR, compounds 5 and 6 show low affinity relative to RA for binding to the nuclear retinoic acid receptors (RAR), which mediate most of the actions of natural retinoids.[9] Unlike compound 2, 4-HPR causes apoptosis in numerous cancer cell lines.[11] Thus the mode of action of these synthetic retinoids remains unclear.

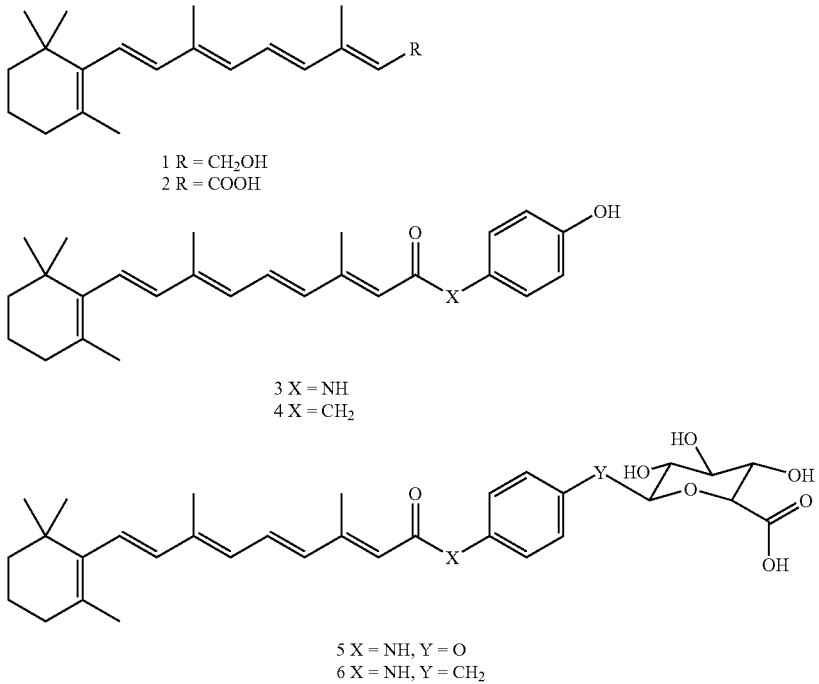

1 R = CH$_2$OH
2 R = COOH

3 X = NH
4 X = CH$_2$

5 X = NH, Y = O
6 X = NH, Y = CH$_2$

While 4-HPR (compound 3) has been shown to be an effective chemopreventative and therapeutic agent, some of its effects may be attributed to in vivo hydrolysis of the amide bond, liberating RA. To investigate this possibility, an unhydrolyzable analog of 4-HPR, 4-hydroxybenzyl retinone (4-HBR; compound 4) was synthesized. Both compounds 3 and 4 were shown to be equiactive chemotherapeutics in the dimethylbenz[a]anthracene (DMBA)-induced rat mammary tumor model.[12,13] In vitamin A-deficient rats, compound 3, but not compound 4, is hydrolyzed to liberate retinoic acid.[13] Furthermore, 4-HPR (3) but not the C-linked analog (4) induces CYP26B1 mRNA expression in a RA-like manner in the lungs of vitamin A-deficient rats. Based on the positive chemotherapeutic and apoptotic-inducing activity of compound 4, it appears that hydrolysis of 4-HPR is not required for the therapeutic effect of this retinoid, but rather, the liberation of RA may contribute to its retinoid-based toxic side effects.

4-HPR has been shown to be 100 times less teratogenic than RA and this toxicity may also be caused by the liberation of RA. With the effective antitumor agent 4-HPRCG (compound 6), amide bond hydrolysis may still occur in vivo, thus liberating retinoic acid by similar mechanisms as for 4-HPR. Therefore, an unmet need exists for compounds that exhibit the desirable anti-neoplastic activities of HPRCG, but which are not metabolized in vivo to yield retinoic acid. The present invention is directed to such compounds.

SUMMARY OF THE INVENTION

The invention is directed to compounds of Formula 1:

Formula I

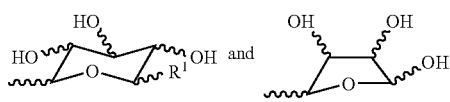

wherein X is $CH_2$; Y is $C_1$-$C_6$ alkylene; and R is selected from the group consisting of hydrogen, $C_1$-$C_6$ alkyl,

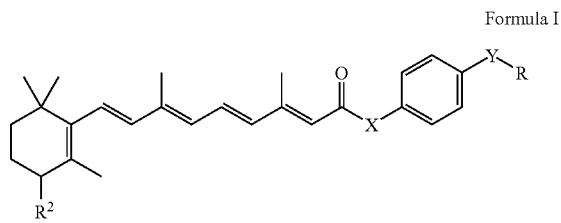

wherein $R^1$ is selected from the group consisting of H, OH, COOH, $C_1$-$C_6$ alkyl, alkenyl, alkynyl, and $C_1$-$C_6$-hydroxyalkyl; $R^2$ is selected from the group consisting of H, OH and =O; and salts thereof The "R" substituent can be in any stereochemical configuration (i.e., D or L; R or S, etc.) as indicated by the wavy bonds depicted in the two structures for "R" shown immediately above. Likewise, the 9,13-dimethyl-substituted alkenylene chain, which is depicted in Formula I in an all-trans conformation, may also include one or more cis double bonds, at any position within the chain, but most notably at the 9 and 13 positions. Thus, the present invention explicitly encompasses compounds of Formula I having any combination of cis or trans double bonds within the alkenylene chain, such as (for example, and not by way of limitation), the 9-cis isomer and the 13-cis isomer:

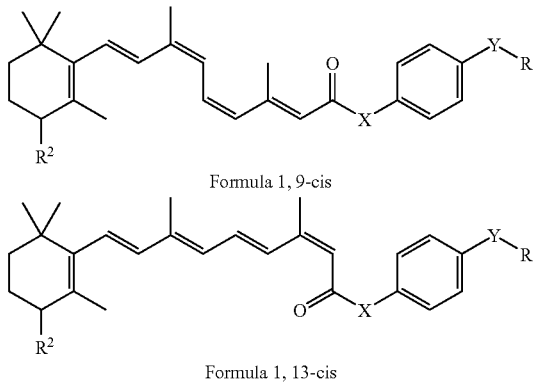

Formula 1, 9-cis

Formula 1, 13-cis

The invention is further directed to pharmaceutical compositions for preventing and/or treating cancer in mammals. The compositions comprise an effective cancer cell growth-inhibiting amount of one or more compounds as described herein (optionally in combination with a pharmaceutically-suitable carrier).

The invention is further directed to a method of preventing and/or treating cancer in mammals. The method comprises administering a cancer cell growth-inhibiting amount of a compound or pharmaceutical composition disclosed herein to a patient in need thereof, including a human patient.

The compounds are useful to prevent and to treat cancer in mammals, including humans. This utility is shown via the results of tumor growth inhibition assays using an accepted in vivo rat model of breast cancer. (See the Examples).

BRIEF DESCRIPTION OF THE DRAWINGS

FIG. 3A is a graph depicting competition of retinoids for [$^3$H]all-trans RA binding to RARβ. ■=4-HPR; □=4-HBRC-Glucuronide; ♦=atRA; Δ=4-HBRCGlucose.

FIG. 3B is a graph depicting competition of retinoids for [$^3$H]all-trans RA binding to RARγ. ■=4-HPR; □=4-HBRC-Glucuronide; ♦=atRA; Δ=4-HBRCGlucose.

DETAILED DESCRIPTION OF THE INVENTION

Figure 1:
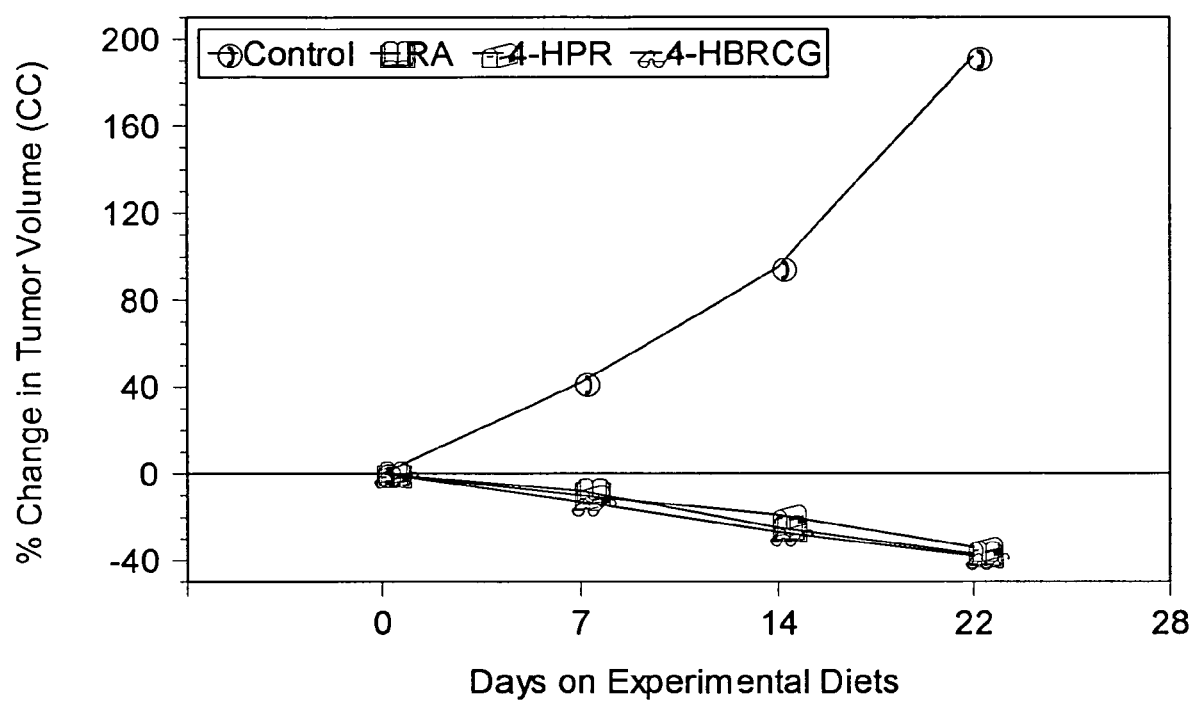
FIG. 1 is a graph depicting the effect of retinoid treatment on time-course changes in DMBA-induced tumor volume in rats.

Abbreviations and Definitions:

The following abbreviations and definitions are used throughout the specification and claims. Terms not given an explicit definition herein are to be interpreted according to their terms as understood in the fields of organic chemistry, pharmacology, and/or pharmaceutical formulations.

Ac$_2$O=acetic anhydride.
AcOH=acetic acid.
atRA=all-trans retinoic acid.
9-BBN-H=9-borabicyclo[3.3.1]nonane.
BMC=bone mineral content.
Cp=cyclopentadienyl.
DMAP=4-dimethylaminopyridine.
DMBA=dimethylbenz[a]anthracene.
DMF=N,N-dimethylformamide.
DMK=dimethyl ketone, acetone.
dppf=1,1'-bis(diphenylphosphino)ferrocene.
EDTA=ethylenediaminetetraacetic acid.
Et$_3$N=triethylamine.
4-HBR=4-hydroxybenzyl retinone.
4-HBRCG=4-hydroxybenzyl retinone-C-glucuronide.
4-HBRCGlucuronide=4-hydroxybenzyl retinone-C-glucuronide.
4-HBRCGlucose=4-hydroxybenzyl retinone-C-glucose.
HPLC=high-performance liquid chromatography.
4-HPR=N-(4-hydroxyphenyl) retinamide.
4-HPRCG=N-(4-hydroxyphenyl) retinamide-C-glucuronide.
4-HPROG=N-(4-hydroxyphenyl) retinamide-O-glucuronide.
HRMS (ES)=high-resolution mass spectrometry, electrospray ionization.
IR=infrared.
LiHMDS=lithium hexamethyldisilazide.
MeOH=methanol.
MOM=methoxymethyl.
MOMCl=methoxymethylchloride.
mp=melting point.
mRNA=messenger ribonucleic acid.
NMR=nuclear magnetic resonance.
Ph=phenyl.

Pharmaceutically-suitable salts=Any acid- or base-addition salt whose counter-ions are non-toxic to the patient in pharmaceutical doses of the salts, so that the beneficial effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isothionates, di-p-toluoyl-tartrates, methane-sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like.

Q—PCR=quantitative polymerase chain reaction.
RA=retinoic acid.
RAR=retinoic acid receptors.
RBP=retinol-binding protein.
rt=room temperature.
RXR=retinoid X receptor.
SEM=standard error of the means.
TBAF=tetrabutylammonium fluoride.
TBDMSCN=t-butyldimethylsilylcyanide.
TEMPO=2,2,6,6-tetramethyl-1-piperidinyloxy free radical.
THF=tetrahydrofuran.
TMS=tetramethylsilane.

Introduction:

To eliminate the possibility of enzymatic hydrolysis to release retinoic acid, the present invention is directed to a C-linked compound (4-HBRCG; compound 7) and analogs thereof In 4-HBRCG, the amide bond of 4-HPRCG is replaced with a methylene group to yield the fully C-linked derivative of 4-HPR-O-glucuronide, compound 7. The synthesis and therapeutic evaluation of 4-HBRCG and analogs thereof are disclosed and claimed herein.

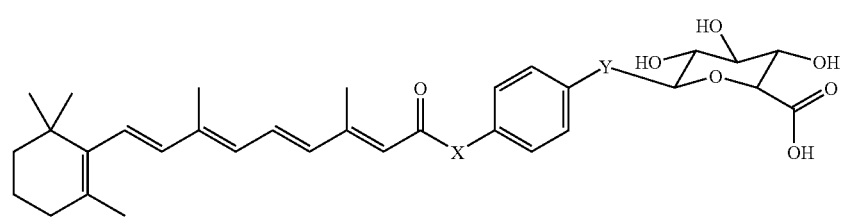

X = Y = CH$_2$

4-HBRCG

Chemistry:

The recently reported improved synthetic route to 4-HPRCG employs a Suzuki coupling reaction between an exoanomeric methylene sugar and an aryl bromide.[10] This methodology, originally developed by Johnson and coworkers,[14,]

gives ready access to β-arylmethyl-C-glycosides. Using the same chemistries, with modifications noted herein, the key benzyl bromide 14 was synthesized (see Scheme 1). Using a convergent approach, an umpolung derivative of retinal was then alkylated with the benzyl bromide to obtain the carbon skeleton of the final target, 4-HBRCG (see Scheme 2).

Starting from readily available δ-D-gluconolactone (compound 8), hydroxyl protection using mild conditions with methoxymethylchloride (MOMCl) and diisopropylethylamine gives the protected lactone 9 (Scheme 1). Olefination using Petasis reagent[16,17] gives the known exoanomeric methylene sugar 10 in good yield.[14] Hydroboration of the exocyclic olefin with 9-borabicyclo[3.3.1]nonane (9-BBN-H), followed by a Suzuki coupling with p-bromobenzyl alcohol, gives exclusively the β-arylmethyl-C-glucoside, compound 11. Previous reports show this reaction is stereoselective.[10,15,18] The benzyl alcohol was easily protected to yield the methyl ether 12. To obtain the glucuronide, the MOM groups were cleaved in acid and the primary alcohol was selectively oxidized to the carboxylate using 2,2,6,6-tetramethyl-1-piperidinyloxy free radical (TEMPO).[19,20] Typically, TEMPO is used catalytically. However, these conditions resulted in nonselective oxidation, yielding mixtures of benzylic ketones. Variations in the time, temperature, base, amount of TEMPO, amount of sodium hypochlorite, and order of addition were attempted without any success in cleanly generating compound 13. From the inventors' past experience, other oxidatively sensitive, sugar-type molecules can undergo selective oxidations when excess TEMPO is used.[21] When excess TEMPO, KBr, and NaClO are premixed in a NaHCO3 solution, deprotected 12 was added and selectively oxidized, efficiently yielding the 6-position carboxylate. Methylation of the carboxylate, followed by acetylation of the remaining alcohols, gives the protected C-aryl-glucuronide 13 in good yield over four steps. Benzylic methyl ethers can be displaced by bromide using hydrobromic acid[22,23] and when exposed to HBr in acetic acid, methyl ether 13 smoothly gave the key benzyl bromide C-glucuronide intermediate 14. This surprisingly facile reaction yielded a very stable benzyl bromide, which was isolated by crystallization.

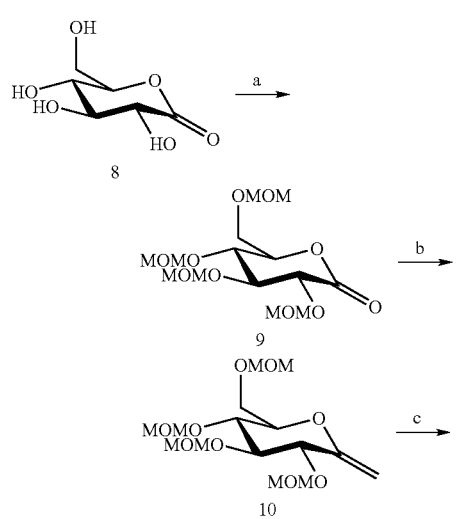

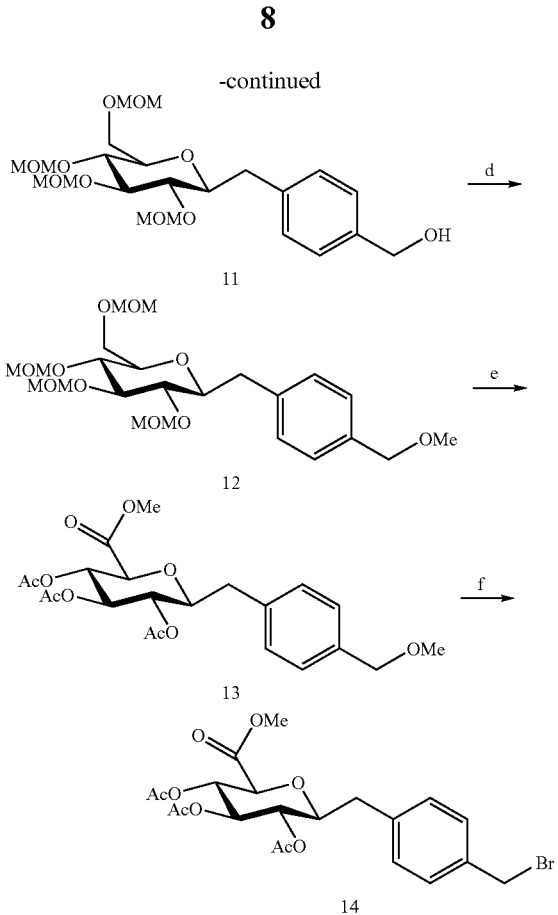

REACTION SCHEME 1

Reagents and conditions for Scheme 1: (a) MOMCl, (i-Pr)2NEt, Bu4NI, CH2Cl2, 48 h, 83%; (b) Cp2Ti(CH3)2, PhCH3, 70° C., 18 h, 87%; (c) (i) 9-BBN-H, THF, reflux, 6 h; (ii) PdCl2(dppf), 3 M K3PO4, DMF, p-bromobenzyl alcohol, 18 h, 67%; (d) (i) NaH, THF, 1.5 h; (ii) CH3I, 18 h, 90%; (e) (i) 6 N HCl, MeOH, 18 h; (ii) TEMPO, NaClO, KBr, NaHCO3, 0° C., 45 min; (iii) CH3I, DMF, 20 h; (iv) Ac2O, pyridine, DMAP, 18 h, 82%; (f) HBr, AcOH, 18 h, 86%.

The next step in this route was the key alkylation of electrophile 14 with a retinal anion equivalent (see Scheme 2). The most suitable umpolung strategy for the chemically sensitive retinal is to employ the protected cyanohydrin derivative,[24] and more particularly the silylcyanohydrin[25] of retinal. The trimethyl-silylcyanohydrin of retinal was first revealed and used in the synthesis of 4-HBR.[12,26] Retinal (compound 15, Scheme 2) exposed to t-butyldimethylsilylcyanide (TBDMSCN) with catalytic Et3N gave chromatographically stable cyanohydrin 16. In the alkylation reaction, the TBDMS-cyanohydrin was deprotonated with LiHMDS and followed by addition of bromide 14. Subsequent chromatography of the alkylated TBDMS-protected product 17 allowed for recovery of the valuable unreacted bromide. Treatment of the alkylated product with fluoride unmasked the ketone to give the penultimate material 18. Using model reactions, substantial efforts were undertaken to improve the yield of the alkylation reaction. Efforts included comparing TMS- and TBDMS-silylcyanohydrin reactivities, employing different bases, and changing the stoichiometry, temperature, and time. Even though recovery of unreacted bromide 14 was important, yields of 17 remained modest due to sensitivities of the polyene retinoid reactant. Lastly, careful deprotection of the acetates and saponification of the methyl ester gave the final target, 4-HBRCG (7). Using this synthetic route, more than 2 grams of 4-HBRCG were produced to facilitate the animal studies and in vitro assays disclosed herein.

Biological Results and Discussion:

Preliminary evaluation of the mammary tumor chemotherapeutic activity of 4-HBRCG (7) was conducted, and its toxicity profile was also assessed. As previously described,[7,12] tumor-bearing female rats (treated ca. 50 days earlier with 7,12-dimethylbenz(a)anthracene [DMBA]) were fed the con-

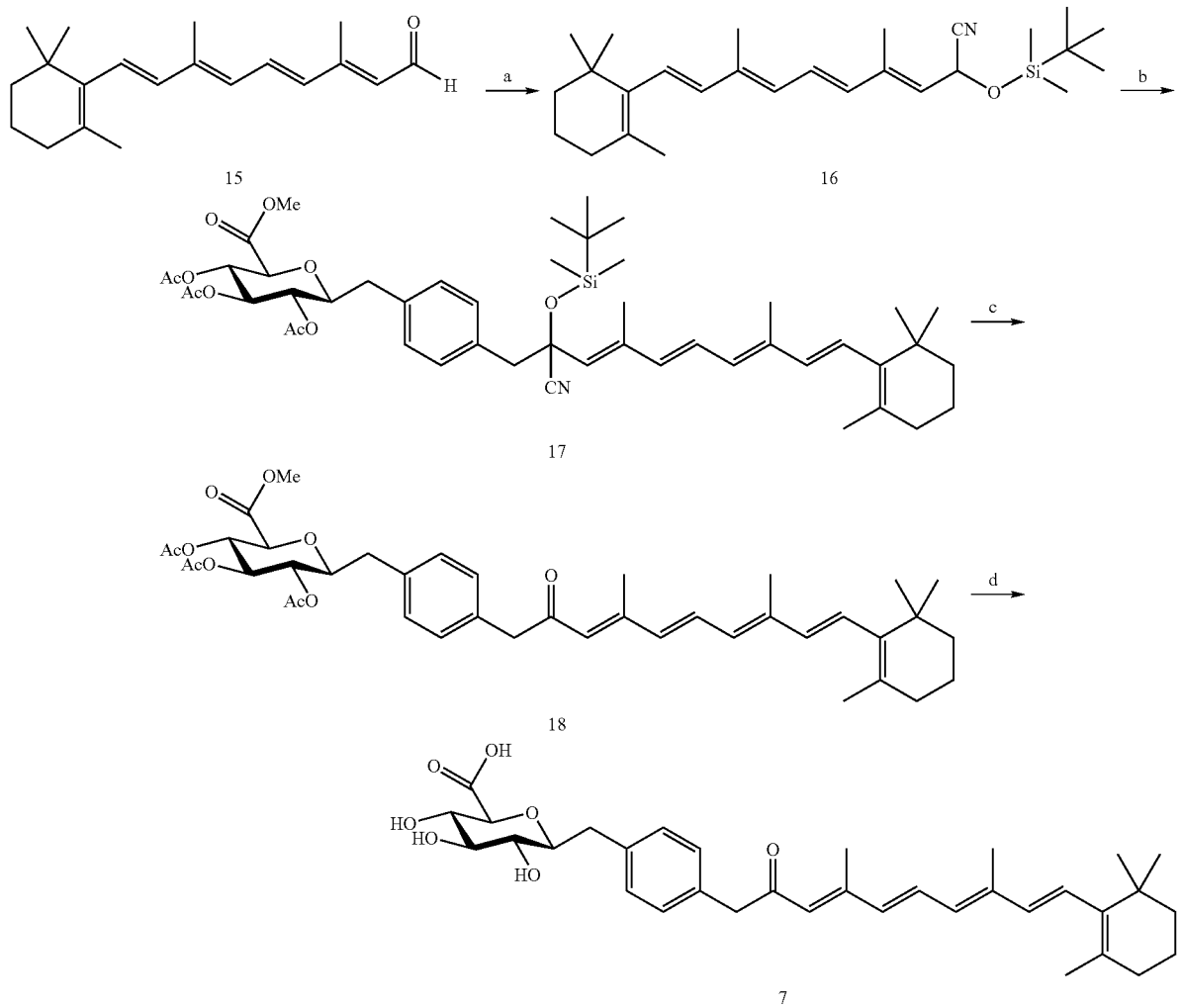

REACTION SCHEME 2

Reagents and conditions for Scheme 2: (a) TBDSMCN, Et$_3$N, CH$_2$Cl$_2$, 20 h, 78%; (b) (i) LiHMDS, THF, −78° C., 30 min; (ii) 14, THF, −78° C., 3 h, 47%; (c) TBAF, THF, 1 h, 75%; (d) (i) K$_2$CO$_3$, MeOH, 4° C., 20 h; (ii) KOH, MeOH, 4° C., 20 h, 82%.

The other analogs disclosed herein can be fabricated by starting with the appropriate initial reactants and then by following the same reaction routes and chemistries described immediately above and in the Examples. For example, the analogous 9-cis and 13-cis precursors can be obtained commercially from Sigma-Aldrich Chemicals (St. Louis, Mo.).

To fabricate the compounds wherein R$^2$ is hydroxy or a double-bonded oxygen (i.e., the 4-hydroxy and 4-oxo derivatives), the 4-hydroxy and 4-oxo retinal reactants can be made using the methods described by Curley & Carson.[45]

trol or retinoid-containing diets (RA (2), 4-HPR (3) or 4-HBRCG (7)) at 2 mmole/kg diet for 22 days. As shown in Table 1, compound 7 is as effective as 2 and 3 in reducing tumor volume (30-40% reduction), whereas control group tumor volumes increased nearly 200% by 22 days. FIG. 1 shows that the time course change in tumor volumes was similar for all three treatment retinoids. Likewise, the data in Table 2 shows that for compound 7, individual tumors in the group responded similarly to the tumors in the other retinoid treated groups.

Of particular note, 4-HBRCG (7) showed evidence of greatly reduced toxicity relative to both RA (2) and 4-HPR (3). As shown in Table 3, during the feeding period, only RA caused a significant reduction in normal body weight gain, a common sign of retinoid toxicity. Perhaps of even greater importance, 4-HBRCG caused a much smaller reduction than did either 4-HPR or RA in plasma retinol levels. It is well known that both RA[27] and 4-HPR[3] can reduce circulating levels of blood retinol. The 4-HPR-induced reduction in plasma retinol has been show to produce impaired dark adaptation, and is the single-most important factor limiting the doses of 4-HPR that have been used in human clinical trials.[28] Because 4-HBRCG fed at 2 mmol/kg diet did not produce any significant reduction in blood retinol, whereas the same amount of 4-HPR did, compound 7 can be administered at relatively higher doses compared to 3 before the risk of night blindness is incurred.

While not being limited to any particular underlying biological mechanism, the reason that 4-HBRCG (7) shows no significant lowering of blood retinol levels may be related to the manner in which it is distributed in vivo (see Table 4). 4-HPR is known to reduce blood retinol levels by competing for binding to the serum retinol-binding protein, RBP.[3,29] Interestingly, both 4-HPR and the related analog, 4-HBR, show equivalent binding to RBP, yet 4-HBR does not lower blood retinol levels.[12] It should be noted that 4-HBR circulates in the blood at lower levels compared to 4-HPR when administered in equimolar quantities.[12] Thus, at least with respect to compounds 3 and 4, blood retinol levels are inversely related to the concentration of 4-HPR that is present in the blood. In the present invention, less 4-HBRCG was present in the plasma at the time the test animals were sacrificed as compared to 4-HPR, suggesting that this decreased plasma concentration may account for the lesser effect of the glucuronide analog 7 on circulating blood retinol levels.

TABLE 1

Effect of retinoid treatment on DMBA-induced rat mammary tumor volume[a]

| Experimental group[b] | Initial tumor volumes (cm³) | Final tumor volume (cm³) | % Change[c] |
|---|---|---|---|
| Control | 0.10 ± 0.05 | 0.29 ± 0.12 | +190[d] |
| Retinoic acid (2) | 0.08 ± 0.03 | 0.05 ± 0.02 | −38[d] |
| 4-HPR (3) | 0.12 ± 0.03 | 0.08 ± 0.02 | −33[d] |
| 4-HBRCG (7) | 0.12 ± 0.06 | 0.08 ± 0.05 | −33[d] |

[a]Value = mean ± SEM
[b]Retinoid doses of 2 mmol/kg diet were fed to animals for 22 days
[c]Change from baseline
[d]Denotes statistical significance, $p < 0.05$

TABLE 2

Effect of retinoid treatment on individual tumors

| Experimental group | Total number of tumors | Complete regression[a] | Partial regression[b] | New tumors | No effect |
|---|---|---|---|---|---|
| Control | 15 | 0 | 0 | 2 | 13 |
| RA (2) | 10 | 1 | 8 | 0 | 1 |
| 4-HPR (3) | 19 | 1 | 15 | 0 | 3 |
| 4-HBRCG (7) | 10 | 2 | 6 | 0 | 2 |

[a]Represents tumors that totally disappeared and could not be palpated
[b]Represents tumors that showed 25-75% decrease in volume

TABLE 3

Effect of dietary retinoid on body weight and plasma retinol level

| Experimental group | % Weight change[a] | Plasma retinol[b]* |
|---|---|---|
| Control | +3 | 0.56 ± 0.10 |
| Retinoic acid (2) | +0.2[d] | 0.26 ± 0.03[e] |

TABLE 3-continued

Effect of dietary retinoid on body weight and plasma retinol level

| Experimental group | % Weight change[a] | Plasma retinol[b]* |
|---|---|---|
| 4-HPR (3) | +3 | 0.21 ± 0.05[e] |
| 4-HBRCG (7) | +3 | 0.40 ± 0.04 |

*Value = Mean + SEM
[a]Relative to baseline body weight over 22 days
[b]Concentration (μg/ml) at day 22 of treatment measured as in ref. 9
[c]Concentration (mg/ml) at day 22 of treatment measured as in ref. 24
[d]$p < 0.05$ for the trend in mean body weight gain relative to other groups
[e]$p < 0.05$ relative to control group

TABLE 4

Terminal plasma drug levels.

| Experimental group | Plasma retinoid concentration[a] |
|---|---|
| Retinoic acid (2) | 0.30 ± 0.10 |
| 4-HPR (3) | 0.67 ± 0.07 |
| 4-HBRCG (7) | 0.10 ± 0.01 |

[a]Concentration (μg/ml) ± SEM at day 22 of treatment

Figure 2A:
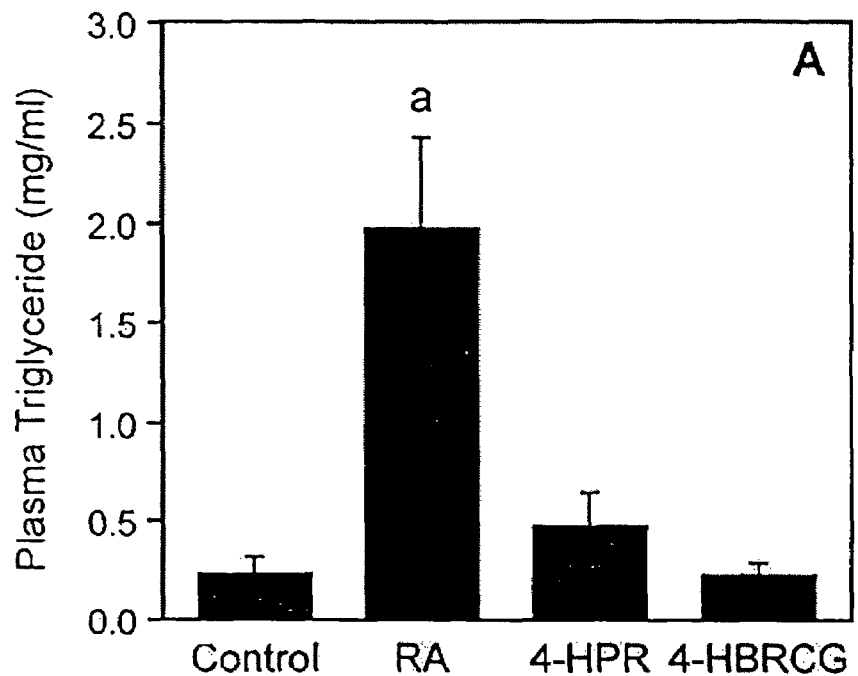
FIG. 2A is a bar graph depicting the effect of retinoid treatment on plasma triglyceride level. The reference "a" designated $p<0.05$ relative to control, 4-HPR, and 4-HBRCG groups.

As shown in FIG. 2A, treatment with RA dramatically increased serum triglyceride concentration, whereas 4-HBRCG did not cause this undesirable effect. An increase in serum triglyceride is a well known side effect of oral RA administration,[30,31] and is mediated by binding to the RAR family.[32] As borne out in human trials, 4-HPR is clearly less potent than RA in producing this side effect.[5] It is possible that hydrolysis of 4-HPR may have accounted for the small but insignificant increase upon feeding of this retinoid in the present work, whereas the non-hydrolyzable 4-HBRCG showed no propensity to increase serum triglyceride levels.

Figure 2B:
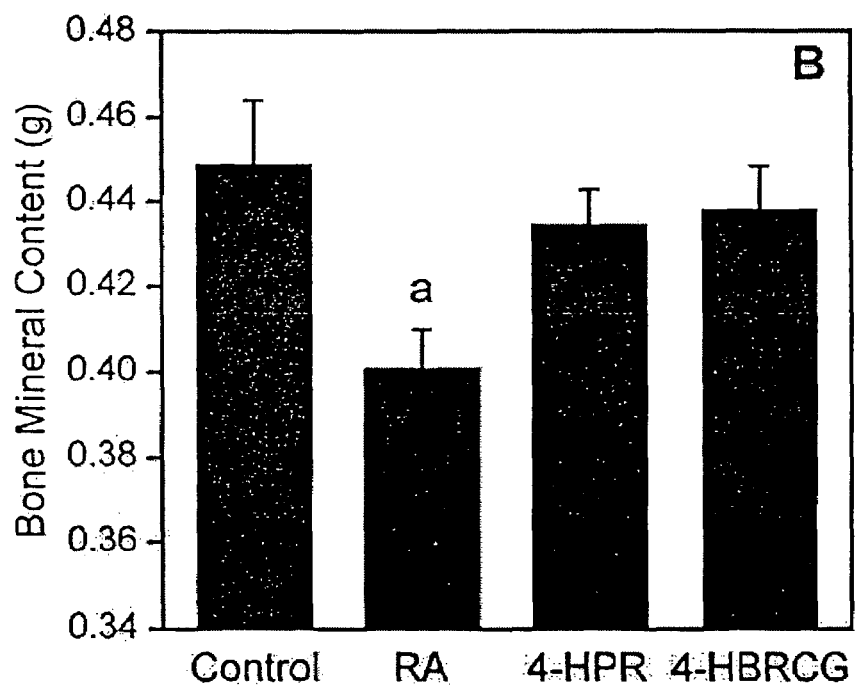
FIG. 2B is a bar graph depicting the effect of retinoid treatment on bone mineral content. Values are mean+SEM. The reference "a" designated $p<0.05$ relative to the control group.

Skeletal abnormalities are another adverse effect of high-dose retinoid therapy.[33-35] In order to determine the extent of any similar effect for 4-HPR and the analog 7, the bone mineral content (BMC) of the femur of animals was measured at the end of the feeding study. As expected, RA produced a significant reduction in femur BMC as compared to control animals (see FIG. 2B), whereas the groups receiving either 3 or 7 showed no such effect. In an early clinical study of women with early breast cancer receiving 4-HPR, a trend toward an increase in bone resorption markers was noted.[36] Although not significant, this suggests that a 4-HPR analog such as 4-HBRCG that cannot liberate RA might be advantageous in minimizing bone risk.

As with 4-HPR and other related analogs (5 and 6), 4-HBRCG binds poorly to the retinoic acid receptors β and γ (RARβ and RARγ) (see FIGS. 3A and 3B). 4-HPR was nearly 3000 times less potent than all-trans retinoic acid (atRA) in competing for [³H]atRA binding to the RARβ, and 2500 times less able to compete for binding to the RARγ.[9,37] In the present work 4-HBRCG also showed only weak RAR binding (300 times and 1400 times less potent than atRA in binding to RARβ and RARγ, respectively). 4-HBRCG at concentrations up to $10^{-4.5}$ M showed similar poor binding to the RARα (data not shown). Furthermore, 4-HBRCG at concentrations up to $10^{-4.5}$ M showed almost no competition for [³H]9-cis RA binding to the RXR (data not shown). Similar to 4-HBRCG, the 4-HBRCGlucose analog (23) also binds poorly to the RARβ and RARγ (see FIGS. 3A and 3B, respectively), and RARα and RXRγ (data not shown).

Figure 4:
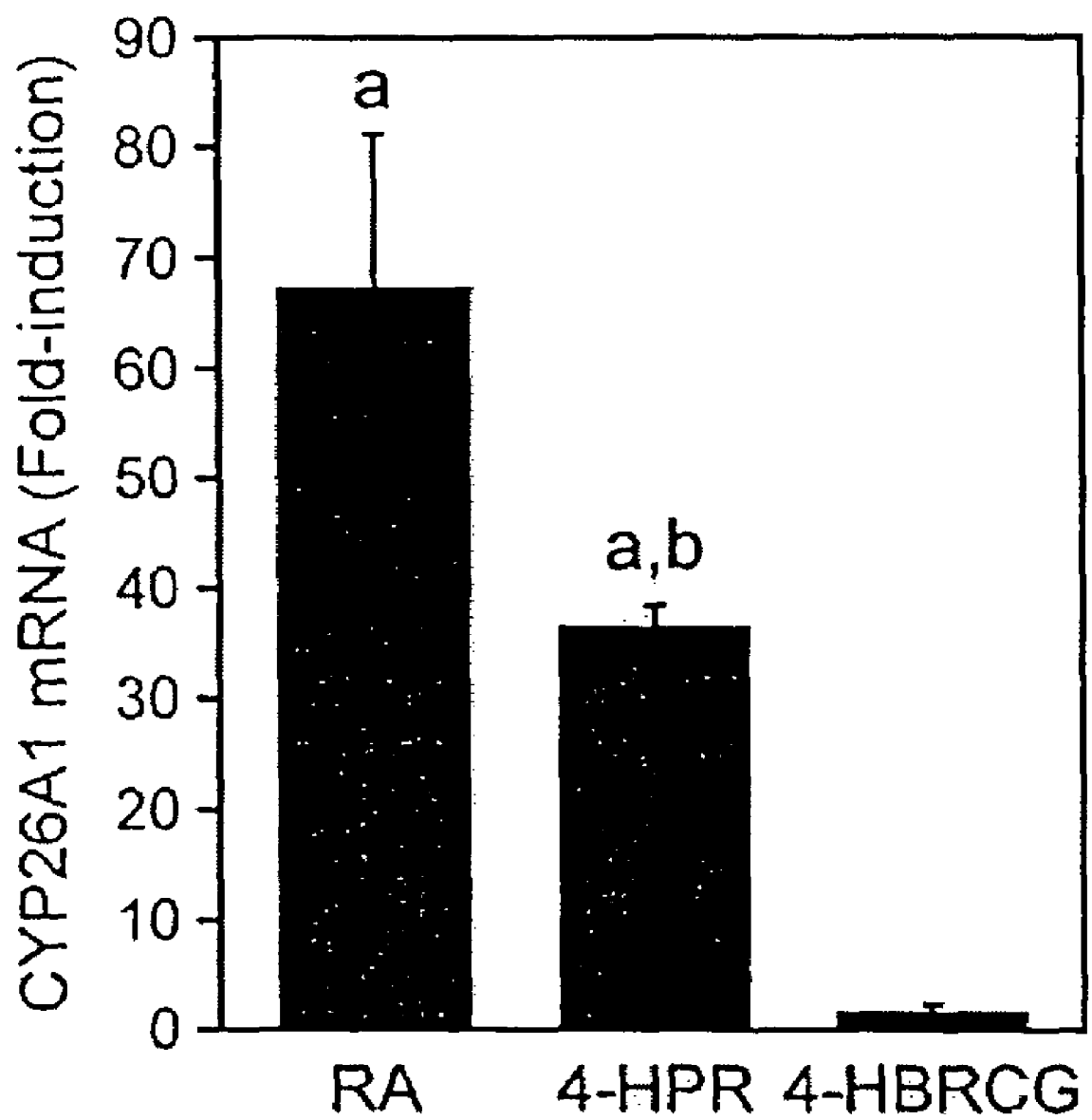
FIG. 4 is a bar graph depicting induction of CYP26A1 mRNA in the liver of retinoid-fed animals relative to the control group. Values are mean+SEM. Reference "a" designated $p<0.05$ relative to control and 4-HBRCG groups; reference "b" designates $p<0.05$ relative to the RA-fed group.

To evaluate the ability of retinoids to activate RAR-mediated gene transcription in vivo, the induction of CYP26 was measured at sacrifice in liver and lung. RA was highly effective in inducing CYP26A1 mRNA in the liver (67-fold above control; see FIG. 4) and CYP26B1 in the lung (46-fold above control; data not shown). 4-HPR also showed significant activity in inducing the CYP26 mRNAs in liver and lung (37- and 20- fold for CYP26A1 and CYP26B1, respectively, compared to control), whereas 4-HBRCG did not induce these cytochrome p450 mRNAs. RA has been shown to induce the CYP26A1 mRNA via binding to RARs and to direct interaction of the liganded RAR/RXR heterodimer with a retinoic acid response element in the promoter region of this RA-responsive gene.[38,39] It has also been shown previously that RA, and to a lesser extent 4-HPR, induces the expression of CYP26B1 mRNA in lungs of vitamin A-deficient rats.[13] The fact that neither compound 3 nor compound 7 show particularly strong binding to the RARs, coupled with the finding that 4-HBRCG actually shows enhanced affinity compared to 4-HPR for the RARs yet does not induce gene expression, argues against a direct interaction of 4-HPR with the receptor as a mechanism to explain its ability to induce these mRNAs. Rather, hydrolysis of 4-HPR to atRA may account for this induction. It has been shown previously that 4-HPR given orally to vitamin A-deficient rats generates RA in plasma that is detectable by HPLC.[13] The lack of induction of RAR-mediated gene transcription by 4-HBRCG in vivo thus supports the conclusion that direct binding of 7 to RARs does not occur at the retinoid levels fed in the present work, and further indicates that RA-mediated toxicities should be less of a problem with the present compounds as compared to 4-HPR.

Although the toxicity of 4-HPR has been reported to be reduced compared to RA, the spectrum of toxicities encountered are similar.[40] Thus, 4-HBRCG shows significant improvement in the therapeutic window compared to the natural hormone, RA, for all measures of toxicity studied here (weight loss, elevation of serum triglyceride, reduction in bone mineral content, reduced blood retinol, and induction of RAR-mediated gene transcription) and for the latter two measures of toxicity when compared to 4-HPR.

Inhibition of MCF-7 human breast cancer cell growth over an 8-day period was used as a means to assess the activity of 4-HBRCG and the analog 4-HBRCGlucose. Both compounds produced a reduction in the number of live cells at $10^{-5}$ M. See FIG. 5. However, in the case of the 4-HBRCGlucose analog, the majority of the MCF-7 cells were dead at the end of the assay. This result strongly suggests that the glucose analog might be an even more potent compound than 4-HBRCG. Activity in inhibiting MCF-7 cell growth has been shown to be predictive of the potential in vivo chemopreventive/chemotherapeutic activity of these analogs.

Figure 5:
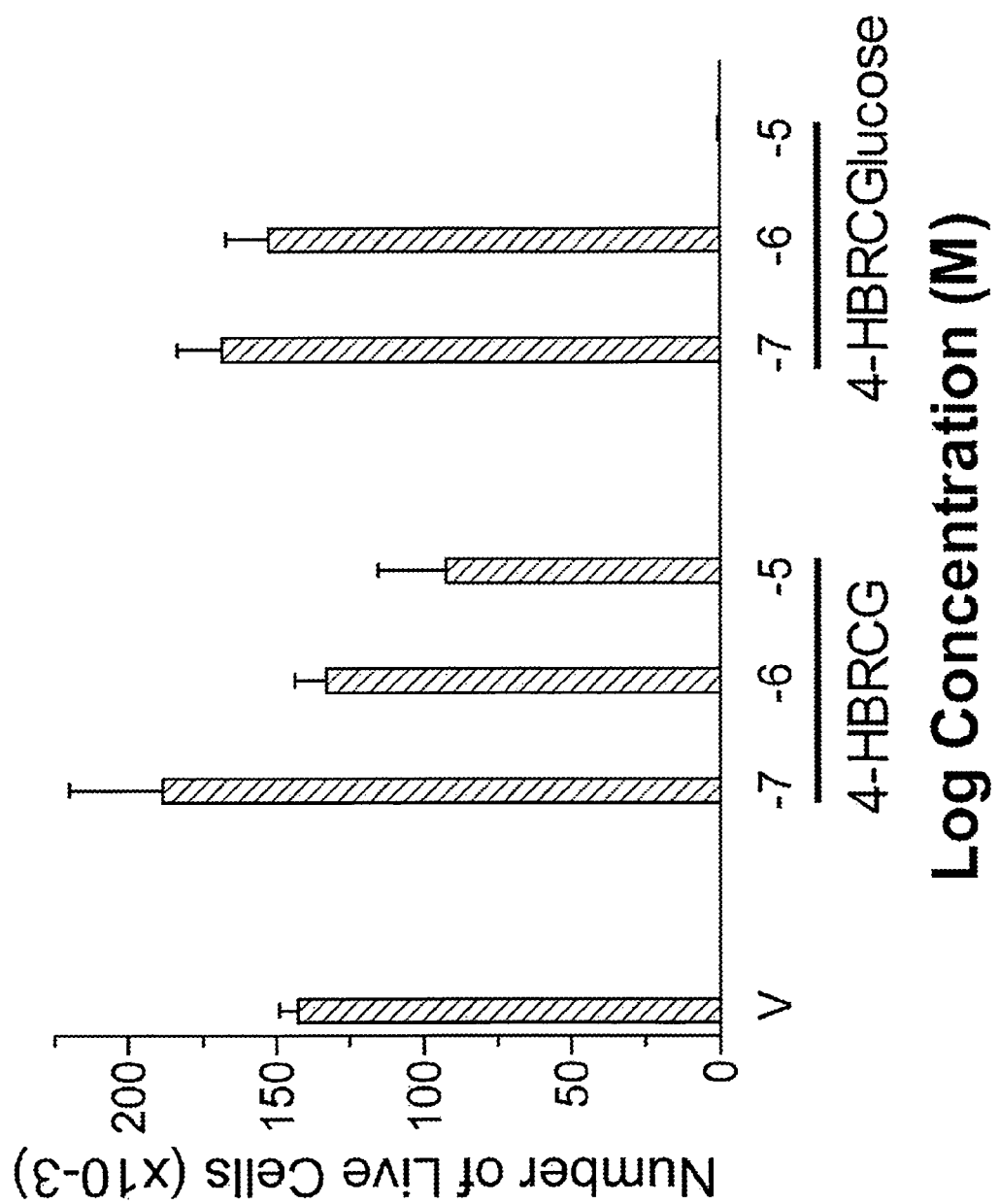
FIG. 5 is a bar graph depicting reduction in live cell number in MCF-7 cells treated with 4-HPRCG or 4-HBRCGlucose, relative to the vehicle control group (V).

In summary, both 4-HBRCG and 4-HBRCGlucose inhibit the growth of MCF-7 human breast cancer cell in culture, as shown in FIG. 5. 4-HBRCG shares the ability with 4-HPR and RA to reduce the size and number of rat mammary tumors. However, a number of the toxic effects shown by the parent retinoids are reduced or eliminated with 4-HBRCG. Thus, these fully unhydrolyzable analogs have a significant utility and advantage as low-toxicity chemopreventive/chemotherapeutic agents for use in mammal, including humans.

Pharmaceutical Compositions:

Another aspect of the invention provides pharmaceutical compositions, for medical use, comprising an active compound, i.e., a Formula I compound or a pharmaceutically-acceptable salt thereof, optionally in combination with an acceptable carrier and optionally in combination with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal or parenteral (including subcutaneous, intramuscular and intravenous) administration.

The formulations may conveniently be presented in unit dosage form and may be prepared by any of the methods well known in the pharmaceutical arts. The term "unit dosage" or "unit dose" is denoted to mean a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an oil, aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface-active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound of Formula I which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefor such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

Compositions suitable for rectal administration, comprise a suppository, preferably bullet-shaped, containing the active ingredient and pharmaceutically-acceptable vehicles therefor such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefor such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the subject compounds are preferably utilized at concentrations of from about 0.1 to about 10% by weight.

Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of compounds of Formula I are preferably utilized at concentrations of from about 0.1% to 5.0% by weight applied to a dressing.

Compositions suitable for administration by inhalation include formulations wherein the active ingredient is a solid or liquid admixed in a micronized powder having a particle size in the range of about 5 microns or less to about 500 microns or liquid formulations in a suitable diluent. These formulations are designed for rapid inhalation through the oral passage from conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, e.g., diluents, buffers, flavoring agents, colorants, binders, surface-active agents, thickeners, lubricants, suspending agents, preservatives (including antioxidants) and the like.

The amount of compound of Formula I required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose is in the range of about 0.05 to about 200 mg/kg body weight per day, preferably in the range of about 1 to about 70 mg/kg per day, calculated as the non-salt form of Formula I. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

In general, the pharmaceutical compositions of this invention contain from about 0.5 mg to about 1.5 g active ingredient per unit dose and, preferably, from about 7.5 to about 1000 mg per unit dose. If discrete multiple doses are indicated, treatment might typically be 100 mg of a compound of Formula I given from two to four times per day.

The compounds according to the present invention may be administered prophylactically, chronically, or acutely. For example, such compounds may be administered prophylactically to inhibit the formation of cancers in the subject being treated. The subject compounds may also be administered prophylactically to patients suffering a primary cancer to prevent the occurrence of metastatic cancers. In addition to the prevention of primary and metastatic cancers, chronic administration of the subject compounds will typically be indicated in treating recurring cancers. Acute administration of the subject compounds is indicated to treat, for example, aggressive cancers prior to surgical or radiological intervention.

EXAMPLES

The following Examples are included solely to provide a more complete description of the invention disclosed and claimed herein. The Examples do not limit the scope of the invention in any fashion.

Synthesis:

General methods: Anhydrous THF and $CH_2Cl_2$ were obtained using distillation from sodium benzophenone ketyl and calcium hydride, respectively. Sigma-Aldrich (Milwaukee, Wis.) supplied starting materials and reagents. Cambridge Isotopes Laboratories (Cambridge, Mass.) supplied isotope labeled reagents. All reactions and handling of retinoid-containing compounds were done under gold fluorescent lights. Thin-layer chromatography was performed on Merck (Gibbstown, N.J.) silica gel 60 $F_{254}$ aluminum plates. Column chromatography was performed with Merck silica gel 60 and reverse phase flash chromatography with Merck Lichroprep® RP-18. Analytical HPLC was done on Beckman Instruments (San Ramon, Calif.), with pump component 127 and detector module 166, equipped with a Metachem Polaris (Varian), 5 µm C-18, 250×4.6 mm column. All retinoids were detected at a wavelength of 350 nm. Melting points were determined using a Thomas-Hoover (Philadelphia, Pa.) capillary apparatus and are uncorrected. Optical rotations were conducted on a Perkin-Elmer (Wellesley, Mass.) 241 polarimeter and reported in mol·$dm^{-1}$·$gram^{-1}$. Ultraviolet spectra were recorded on a Beckman Instruments DU-40 spectrophotometer. Infrared spectra were recorded as films on silver chloride plates using a Nicolet (Madison, Wis.) Protege 460 spectrophotometer. NMR spectra were recorded on a Bruker (Billerica, Mass.) DRX 400 spectrometer. Mass spectra were recorded on a Micromass (Milford, Mass.) QTOF Electrospray mass spectrometer.

2,3,4,6-tetra-O-(methoxymethyl)-D-gluconic acid-δ-lactone (9). To a flame-dried flask under argon atmosphere was added δ-gluconolactone (8) (7.38 g, 41.4 mmol) and $CH_2Cl_2$ (400 mL). Upon cooling the suspension with an ice bath, diisopropylethylamine (57.6 mL, 331 mmol) was added dropwise, followed by careful addition of chloromethyl methyl ether (50 g, 621 mmol) via an addition funnel. A significant amount of white smoke formed in the reaction vessel. Solid tetrabutylammonium iodide (50 g, 134 mmol) was added and the solution was allowed to warm to room temperature (hereinafter "rt"). The reaction stirred in the dark for 48 h upon which the solution gradually turned red. After cooling the vessel to 0° C., saturated aqueous $NH_4Cl$ (75 mL) was added. The contents were then diluted with water and the layers separated. The organic layer was washed with brine and the combined aqueous layers were extracted with $CH_2Cl_2$ (3×). The combined organic layers were dried ($MgSO_4$), filtered, and concentrated. The solids were then triturated with ether (4×) and the ether was concentrated. The resultant oil was chromatographed on silica gel (1:1 hexanes/ethyl acetate) to afford 12.04 g (83%) of clear oil. $[\alpha]_D$ 118.4 (c 2.15, $CH_2Cl_2$); IR ($cm^{-1}$) 2948 (s), 2885 (s), 1757 (s), 1464 (m), 1443 (m), 1213 (s), 1150 (s), 1035 (s), 912 (m); $^1H$ NMR ($CDCl_3$) δ 3.36-3.42 (m, 12H), 3.77 (dd, 1H, J=3.8, 11.3 Hz), 3.82 (dd, 1H, J=2.8, 11.3 Hz), 3.99-4.05 (m, 2H), 4.29 (d, 1H, J=6.6 Hz), 4.55-4.56 (m, 1H), 4.65 (s, 2H), 4.69-4.92 (m, 7H); $^{13}C$ NMR ($CDCl_3$) 55.42, 56.05, 56.11, 56.22, 66.12, 73.69, 74.77, 78.43, 96.56, 96.66, 96.78, 96.91, 97.13, 168.70; HRMS (ES) calcd for $C_{14}H_{26}O_{10}$ (M+Na) 377.1424, found 377.1408.

Dimethyl titanocene, $Cp_2Ti(CH_3)_2$ (Petasis' reagent). To a flame-dried flask under argon atmosphere was added titanocene dichloride (14.63 g, 58.8 mmol) and absolute ether (300 mL), which was cooled to 10° C. Methyl lithium (100 mL, 140 mmol, 1.4 M) was carefully added dropwise via an addition funnel in the dark. The cold bath was removed and the red solution was allowed to stir for 10 min. The solution was then cooled to 0° C. and ice water (25 mL) was carefully added to quench the unreacted methyl lithium. The layers were separated and the aqueous layer extracted with ether (2×). The combined organic layers were dried ($Na_2SO_4$) under argon for 1 h and concentrated in the dark at 20° C. to give 12.4 g of orange solid. Dry toluene (100 mL) was added and the reagent was stored at 4° C. and used without characterization.

2,6-Anhydro-1-deoxy-3,4,5,7-tetra-O-(methoxymethyl)-D-gluco-hept-1-enitol (10). To a flame-dried flask under argon atmosphere was added the sugar lactone 9 (10.05 g, 28.4 mmol) dissolved in dry toluene (140 mL) via an addition funnel. The toluene solution of dimethyl titanocene (12.4 g, 59 mmol) was then added dropwise via an addition funnel to give a red solution. The flask was then equipped with a reflux condenser and heated to 70° C. and let stir in the dark for 18 h. The resultant black solution was cooled and poured into hexanes (~500 mL). A precipitate formed and was filtered through celite. The supernatant was concentrated to yield a red oil which was chromatographed on silica gel (4:1 then 2:1 hexanes/ethyl acetate) to afford 8.66 g (87%) of yellowish oil. $[\alpha]_D$ 46.8 (c 2.33, $CH_2Cl_2$); IR ($cm^{-1}$) 2940 (m), 2895 (m), 1750 (w), 1440 (w), 1154 (s), 1032 (s), 918 (m); $^1$H NMR (DMK-$d_6$) δ 3.31-3.37 (m, 12H), 3.64-3.71 (m, 2H), 3.78-3.83 (m, 2H), 3.88-3.89 (m, 1H), 4.12 (d, 1H, J=5.4 Hz), 4.35 (s, 1H), 4.51 (s, 1H), 4.62 (s, 2H), 4.66-4.84 (m, 6H); $^{13}$C NMR (DMK-$d_6$) δ 55.15, 55.87, 56.04, 56.19, 67.50, 75.42, 76.68, 77.36, 81.08, 93.43, 95.35, 97.23, 97.64, 97.81, 156.39; HRMS (ES) calcd for $C_{15}H_{28}O_9$ (M+Na) 375.1631, found 375.1628.

2,6-Anhydro-1-deoxy-1-[4-(hydroxymethyl)phenyl]-3,4,5,7-tetra-O-(methoxymethyl)-D-glycero-D-gulo-heptitol (11). To a flame-dried flask under argon atmosphere was added the exocyclic olefin 10 (3.75 g, 10.6 mmol) dissolved in dry THF (100 mL). 9-BBN-H (53.2 mL, 26.6 mmol, 0.5 M) was added via addition funnel. The flask was then equipped with a reflux condenser, heated to 75-80° C., and refluxed for 4.5 h. The mixture was cooled to rt, then $K_3PO_4$ (10 mL, 3 M) was added and allowed to stir for 10 min. p-Bromobenzyl alcohol (3.98 g, 21.3 mmol) and $PdCl_2(dppf)$ (0.686 g, 0.85 mmol) dissolved in DMF (100 mL) was added via addition funnel and stirred for 18 h. The reaction was diluted with water and ether, and then the layers were separated. The organic layer was washed with water and brine. The combined aqueous layers were extracted with ether (3×). The organic layers were combined, dried (MgSO4), concentrated, and chromatographed (1:1 then 1:2 hexanes/ethyl acetate) to afford 3.29 g (67%) of orange oil. $[\alpha]_D$ −26.2 (c 1.15, DMK); IR ($cm^{-1}$) 3470 (w), 2932 (m), 2887 (m), 1692 (m), 1444 (w), 1150 (s), 1101 (s), 1024 (s), 918 (m); $^1$H NM (DMK-$d_6$) δ 2.60 (dd, 1H, J=9.4, 14.4 Hz), 3.18-3.42 (m, 5H), 3.25 (s, 3H), 3.35 (s, 3H), 3.40 (s, 3H), 3.44 (s, 3H), 3.54-3.61 (m, 2H), 3.73 (dd, 1H, J=1.8, 11.3 Hz), 4.51-4.58 (m, 4H), 4.70 (d, 1H, J=6.5 Hz), 4.77-4.85 (m, 4H), 4.93 (d, 1H, J=6.5 Hz), 7.25 (s, 4H); $^{13}$C NMR (DMK-$d_6$) δ 38.35, 55.04, 56.45, 56.55, 64.44, 64.57, 67.42, 77.97, 79.07, 80.32, 81.63, 84.83, 97.20, 99.01, 99.19, 99.32, 127.15, 130.11, 138.75, 141.03; HRMS (ES) calcd for $C_{22}H_{36}O_{10}$ (M+Na) 483.2206, found 483.2188.

2,6-Anhydro-1-deoxy-1-[4-(methoxymethyl)phenyl]-3,4,5,7-tetra-O-(methoxymethyl)-D-glycero-D-gulo-heptitol (12). To a flame-dried flask under argon atmosphere was added the C-glycoside benzyl alcohol 11 (2.44 g, 5.3 mmol) dissolved in dry THF (100 mL). Sodium hydride (0.63 g, 26.5 mmol) was added to the flask and the suspension stirred for 1.5 h. Iodomethane (4.5 g, 31.7 mmol) dissolved in THF (10 mL) was cannulated into the reaction mixture and allowed to stir for 18 h. After cooling in an ice bath, water was added carefully to quench excess NaH. The mixture was extracted with ether (3×), the organic layers combined, washed with brine, dried (MgSO4), concentrated, and then chromatographed (1:1 then 1:2 hexanes/ethyl acetate) to give 2.37 g (94%) of clear oil. $[\alpha]_D$ −27.0 (c 4.70, DMK); IR ($cm^{-1}$) 2981 (s), 2883 (s), 1701 (w), 1513 (m), 1444 (m), 1378 (m), 1301 (m), 1158 (s), 1105 (s), 1028 (s), 918 (s); $^1$H NMR (DMK-$d_6$) δ 2.61 (dd, 1H, J=9.4, 14.4 Hz), 3.19-3.42 (m, 5H), 3.24 (s, 3H), 3.30 (s, 3H), 3.35 (s, 3H), 3.40 (s, 3H), 3.44 (s, 3H), 3.54-3.64 (m, 2H), 3.73 (dd, 1H, J=2.6, 13.5 Hz), 4.38 (s, 2H), 4.50 (d, 1H, J=6.4 Hz), 4.54 (d, 1H, J=6.4 Hz), 4.70 (d, 1H, J=6.5 Hz), 4.77-4.85 (m, 4H), 4.93 (d, 1H, J=6.5 Hz), 7.21 (d, 2H, J=8.0 Hz), 7.28 (d, 2H, J=8.0 Hz); $^{13}$C NMR (DMK-$d_6$) δ 33.39, 55.05, 56.47, 56.49, 56.57, 57.97, 67.46, 74.84, 78.00, 79.10, 80.23, 81.66, 84.86, 97.20, 99.01, 99.21, 99.32, 128.15, 130.19, 137.23, 139.45; HRMS (ES) calcd for $C_{23}H_{38}O_{10}$ (M+Na) 497.2363, found 497.2384.

2,6-Anhydro-7-deoxy-7-[4-(methoxymethyl)phenyl]-3,4,5-tri-O-acetyl-L-glycero-L-gulo-heptinoic acid methyl ester (13). The MOM-protected glucoside 12 (2.43 g, 5.12 mmol) dissolved in methanol (500 mL) was placed in a flask at rt. Aqueous HCl (6 N, 26 mL) was added and the solution stirred for 18 h after which the mixture was then concentrated to dryness and set aside. In a separate flask, KBr (2.42 g, 20.38 mmol) and TEMPO (3.19 g, 20.41 mmol) were added to a saturated $NaHCO_3$ solution (400 mL) and stirred for 20 min at 0° C. Aqueous NaOCl (11.2 mL, 1.6-2.0M) was then added and stirred for 10 min. The deprotected sugar was dissolved in saturated $NaHCO_3$ solution (100 mL) and added to the flask with the TEMPO mixture. The total mixture was stirred for 45 min at 0° C. Then the reaction was quenched with EtOH (50 mL) and the contents were washed with ether in a separatory funnel. The aqueous layer was concentrated to dryness and the remaining solid was exhaustively triturated with methanol. The methanol was then concentrated and dried. The dried residue was suspended in DMF (180 mL) and then iodomethane (6.4 g) dissolved in DMF (10 mL) was added and allowed to stir for 20 h under argon at rt. The reaction mixture was then supplemented with acetic anhydride (40 mL), pyridine (20 mL), and DMAP (15 mg) and allowed to stir for 18 h. The reaction mixture was diluted with water and extracted (3×) with ethyl acetate. The organic layers were washed with water, brine, dried (MgSO4), concentrated, and chromatographed (2:1 then 1:1 hexanes/ethyl acetate) to give 1.90 g (82%) of clear oil that solidified upon standing, mp 84-86° C. $[\alpha]_D$ −13.04 (c 1.15, DMK); IR ($cm^{-1}$) 2956 (w), 2818 (w), 1750 (s), 1440 (m), 1370 (m), 1211 (s), 1105 (m), 1028 (m); $^1$H NMR (DMK-$d_6$) δ 1.94 (s, 3H), 1.94 (s, 3H), 1.95 (s, 3H), 2.74-2.81 (m, 1H), 2.90 (dd, 1H, J=3.4, 7.3 Hz), 3.30 (s, 3H), 3.65 (s, 3H), 3.94-3.99 (m, 1H), 4.18 (d, 1H, J=9.8 Hz), 4.38 (S, 2H), 4.90 (t, 1H, J=9.8 Hz), 5.05 (t, 1H, J=9.8 Hz), 5.29 (t, 1H, J=9.8 Hz), 7.22 (s, 4H); $^{13}$C NMR (DMK-$d_6$) δ 20.39, 20.52, 20.60, 38.12, 52.67, 58.03, 70.62, 72.53, 74.09, 74.73, 76.41, 78.62, 128.25, 130.16, 137.43, 137.76, 168.40, 169.89, 170.07, 170.30; HRMS (ES) calcd for $C_{22}H_{28}O_{10}$ (M+Na) 475.1580, found 475.1577.

2,6-Anhydro-7-deoxy-7-[4-(bromomethyl)phenyl]-3,4,5-tri-O-acetyl-L-glycero-L-gulo-heptinoic acid methyl ester (14). To a dry flask equipped with a $CaSO_4$ drying tube was added the C-glucuronide methyl ether 13 (462 mg, 1.02 mmol) along with 30% HBr in acetic acid (5 mL, 25 mmol) at 0° C. The mixture stirred for 30 min and then at rt for 18 h. The mixture was diluted with methylene chloride and then carefully washed with water and saturated $NaHCO_3$ solution. The organic layer was dried (MgSO4), concentrated, and chromatographed (2:1 then 1:1 hexanes/ethyl acetate) to give 440 mg (86%) of white foam, which was crystallized with ether, mp 116-117° C. [α]D -12.03 (c 5.57, DMK); IR (cm$^{-1}$) 3026 (w), 2952 (w), 1754 (s), 1440 (m), 1370 (m), 1215 (s), 1101 (m), 1036 (m); $^1$H NMR (DMK-d$_6$) δ 1.93 (s, 3H), 1.94 (s, 3H), 1.95 (s, 3H), 2.76-2.83 (m, 1H), 2.92 (dd, 1H, J=3.5, 7.3Hz), 3.64 (s, 3H), 3.96-3.99 (m, 1H), 4.20 (d, 1H, J=9.7 Hz), 4.62 (s, 2H), 4.90 (t, 1H, J=9.7 Hz), 5.05 (t, 1H, J=9.7 Hz), 5.29 (t, 1H, J=9.7 Hz), 7.25 (d, 2H, J=8.2 Hz), 7.36 (d, 2H, J=8.2 Hz); $^{13}$C NMR (DMK-d$_6$) δ 20.40, 20.52, 20.63, 34.37, 38.12, 52.69, 70.58, 72.52, 74.04, 76.35, 78.43, 129.88, 130.68, 137.26, 138.67, 168.39, 169.91, 170.09, 170.29; HRMS (ES) calcd for C$_2$H$_{25}$BrO$_9$ (M+Na) 523.0580, found 523.0602.

tert-Butyl-dimethylsilylcyanohydrin of retinal (16). To a flame-dried flask under argon atmosphere was added retinal (15) (1.03 g, 3.62 mmol) dissolved in dry CH$_2$Cl$_2$ (50 mL). A catalytic amount of Et$_3$N (0.1 mL) was added then tert-butyldimethylsilyl cyanide (1.0 g, 7.08 mmol) dissolved in CH$_2$Cl$_2$ (10 mL) was added by cannulation. The reaction stirred for 20 h after which the solution was concentrated, chromatographed (95:5 hexanes/ethyl acetate), dried (Na$_2$SO$_4$) under argon, and subjected to vacuum overnight to give 1.20 g (78%) of orange oil. UV λ$_{max}$=329 nm (ε=49462); IR (cm$^{-1}$) 3042 (w), 2960 (s), 2928 (s), 2850 (s), 2239 (w), 1586 (w), 1472 (m), 1358 (m), 1256 (m), 1105 (s), 963 (s), 832 (s), 775 (m); $^1$H NMR (DMK-d$_6$) δ 0.16 (s, 3H), 0.20 (s, 3H), 0.90 (s, 9H), 1.02 (s, 6H), 1.45-1.48 (m, 2H), 1.58-1.63 (m, 2H), 1.70 (s, 3H), 1.99 (s, 6H), 5.57-5.61 (m, 2H), 6.13-6.23 (m, 3H), 6.38 (d, 1H, J=15.2 Hz), 6.86 (dd, 1H, J=11.3, 15.2 Hz); HRMS (ES) calcd for C$_{27}$H$_{43}$NOSi (M+Na) 448.3012, found 448.2982.

2,6-Anhydro-7-deoxy-7-[4-(retinoylmethyl)-phenyl]-3,4,5-tri-O-acetyl-L-glycero-L-gulo-heptinoic acid methyl ester (18). To a flame-dried flask under argon atmosphere was added THF (40 mL) along with LiHMDS (1.0 M in hexanes, 3.8 mL, 3.8 mmol). The mixture was cooled to –78° C. upon which the silyl cyanohydrin of retinal 16 (1.08 g, 2.54 mmol) in THF (15 mL) was added by cannulation into the flask. The dark red solution was allowed to stir for 30 min at –78° C. The crystalline bromoglucuronide 14 (2.78 g, 5.56 mmol) in THF (15 mL) was cannulated into the flask and the mixture stirred for 3 h at –78° C. after which the solution changed to light red. The reaction was taken out of the cold bath and quenched with a solution of 1 M NH$_4$Cl (10 mL). The mixture was extracted with ethyl acetate (3×) and the organic layers were combined, washed with brine, dried (Na$_2$SO$_4$), filtered, concentrated, and chromatographed (2:1 hexanes/ethyl acetate) to give 1.0 g (47%) of yellow foam 17 and 1.7 g of recovered bromide 14. The alkylated product was taken up in 1% aqueous THF (200 mL) and chilled to 0° C. TBAF (309 mg, 1.18 mmol) was added and the darkened solution stirred 1 h. The reaction was diluted with water and extracted with ethyl acetate (3×). The organic layers were combined, washed with brine, dried (NaSO$_4$), filtered, concentrated, and chromatographed (2:1 hexanes/ethyl acetate) to give 628 mg (35% over two steps) of yellow foam. UVλ$_{max}$=379 nm (ε=36182); HPLC tR=24.0 min, 1 mL/min (85:15 MeOH:H$_2$O both with 10 mM NH$_4$OAc); IR (cm$^{-1}$) 2956 (w), 2924 (w), 2863 (w), 1754 (s), 1672 (w), 1554 (m), 1436 (w), 1362 (w), 1215 (s), 1081 (w), 1028 (w), 971 (w); $^1$H NMR (DMK-d) δ 1.02 (s, 6H), 1.45-1.48 (m, 2H), 1.58-1.62 (m, 2H), 1.69 (s, 3H), 1.90 (s, 3H), 1.93 (s, 3H), 1.95 (s, 3H), 2.01 (s, 3H), 2.03-2.05 (m, 2H), 2.28, (s, 3H), 2.75-2.89 (m, 2H), 3.64 (s, 3H), 3.71 (s, 2H), 3.95-3.98 (m, 1H), 4.19 (d, 1H, J=9.8 Hz), 4.90 (t, 1H, J=9.8 Hz), 5.05 (t, 1H, J=9.8 Hz), 5.29 (t, 1H, J=9.8 Hz), 6.15-6.35 (m, 5H), 7.13-7.20 (m, 5H); $^{13}$C NMR (DMK-d$_6$) δ 13.45, 14.68, 20.41, 20.96, 21.08, 21.15, 22.47, 34.15, 35.41, 38.76, 40.86, 52.25, 53.23, 71.18, 73.09, 74.63, 76.93, 79.13, 126.89, 129.86, 130.73, 130.93, 131.01, 131.47, 133.69, 134.89, 135.11, 137.14, 137.26, 138.95, 139.09, 140.96, 152.68, 168.97, 170.45, 170.64, 170.84, 198.78; HRMS (ES) calcd for C$_4$H$_{52}$O$_{10}$ (M+Na) 727.3458, found 727.3456.

2,6-Anhydro-7-deoxy-7-[4-(retinoylmethyl)-phenyl]-L-glycero-L-gulo-heptinoic acid (7). To a flask was added the protected glucuronide-retinoid conjugate 18 (1.15 g, 1.64 mmol) dissolved in methanol (500 mL) and chilled to 4° C. Potassium carbonate (136 mg, 0.98 mmol) was added and allowed to stir for 20 h. The reaction mixture was concentrated at 25-30° C. to ~200 mL. Adjustment to the original volume with methanol was followed by addition of 1 N KOH (14 ml, 14 mmol). After stirring for 20 h at 4° C., the reaction was warmed and allowed to stir for 5 h at rt. The reaction was then cooled to 0° C. and carefully adjusted to pH 7 with 4 N HCl. The reaction mixture was concentrated at 25-30° C. to ~100 mL, cooled back to 0° C., and the pH carefully adjusted to 3 with 1 N HCl. The suspension was extracted with ethyl acetate and the organic layers were combined, dried (Na$_2$SO$_4$) under argon for 2 h, and carefully concentrated. The residue was chromatographed on reverse phase silica gel (gradient 70:30 to 85:15 methanol/water) to yield 759 mg (82%) of yellow foam, which was stored at –80° C. until needed. UV λ$_{max}$=382 nm (ε=30019); HPLC t$_R$=9.2min (1 mL/min, 85:15 MeOH:H$_2$O both with 10 mM NH$_4$OAc); IR (cm$^{-1}$) 3384 (br), 2920 (s), 1721 (m), 1664 (s), 1550 (s), 1427 (m), 1362 (m), 1232 (w), 1089 (m), 1052 (m), 1102 (s), 967 (w); $^1$H NMR (MeOH-d$_4$) δ 0.94 (s, 6H), 1.38-1.41 (m, 2H), 1.54-1.58 (m, 2H), 1.61 (s, 3H), 1.91 (s, 3H), 1.93-1.96 (m, 2H), 2.20 (s, 3H), 2.60 (dd, 1H, J=8.7, 14.4 Hz), 3.03-3.08 (m, 2H), 3.21-3.29 (m, 2H), 3.37 (t, 1H, J=9.5 Hz), 3.53 (d, 1H, J=9.5 Hz), 3.62 (s, 2H), 6.03-6.25 (m, 5H), 7.02-7.16 (m, 5H); $^{13}$C NMR (MeOH-d$_4$) δ 12.88, 14.45, 20.29, 21.04, 21.93, 29.40, 34.00, 35.25, 38.34, 40.76, 52.11, 73.44, 74.63, 79.28, 80.36, 82.36, 124.37, 126.26, 129.92, 130.19, 130.86, 131.01, 131.12, 134.00, 134.23, 136.82, 138.70, 138.91, 139.04, 141.12, 154.22, 173.26, 201.21; HRMS (ES) calcd for C$_{34}$H$_{44}$O$_7$ (M+Na) 587.2985, found 587.2989.

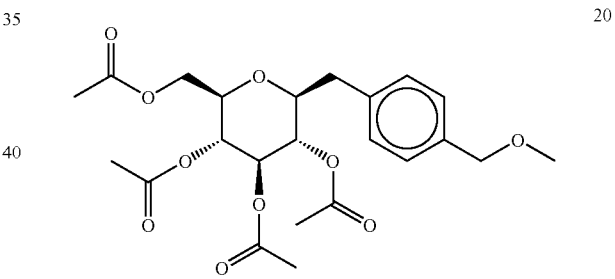

20

2,6-Anhydro-1-deoxy-1-[4(methoxymet6hyl)phenyl]-3,4,5,7-tetra-O-acetyl-D-glycero-D-gulo-heptitol (20). The MOM-protected glucoside 12 (0.643 g, 1.35 mmol) dissolved in methanol (34 mL) was placed in a flask at rt. Aqueous HCL (6 N, 6.7 mL) was added and the solution stirred for 18 h. The mixture was then concentrated to dryness. Acetic anhydride (4 mL) and pyiridine (3 mL) were added to the paste, along with a catalytic amount of DMAP and the mixture was allowed to stir for 18 h at rt. The reaction was diluted with water and extracted with ethyl acetate (3×). The organic layers were combined, washed with water and brine, dried (MgSO$_4$), filtered, concentrated, and chromatographed (1:1 hexanes/ethyl acetate) to give 570 mg (90%) of white solid, mp 120-122° C. [α]D -4.0 (c 0.78, DMK); IR (cm$^{-1}$) 2940 (w), 2862 (w), 1750 (s), 1436 (w), 1370 (m), 1224 (s), 1105 (m), 1032 (m); $^1$H NMR (CDCl$_3$) δ 1.96-2.02 (m, 12H), 2.78 (s, 2H, J=5.8 Hz), 3.36 (s, 3H), 3.52-3.57 (m, 2H), 4.02 (dd, 1H, J=2.3, 12.2 Hz), 4.20 (dd, 1H, J=5.3, 12.2 Hz), 4.40 (s, 2H), 4.92 (t, 1H, J=9.6 Hz), 5.03 (t, 1H, J=9.6 Hz), 5.15 (t, 1H, J=9.6 Hz), 7 16 (d, 2H, J=8.0 Hz), 7.23 (d, 2H, J=8.0 Hz); $^{13}$C NMR (DMK-d$_6$) δ 20.55, 20.57, 20.65, 38.08, 58.02, 63.05, 69.70, 72.81, 74.76, 74.86, 76.05, 78.60, 128.20, 130.21, 137.65, 137.75, 170.04, 170.16, 170.37, 170.59; HRMS (ES) calcd for $C_{23}H_{30}O_{10}$(M+Na) 489.1737, found 489.1727.

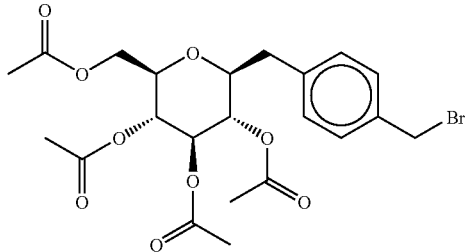

21

2,6-Anhydro-1-deoxy-1-[4-(bromomethyl)phenyl]-3,4,5,7-tetra-O-acetyl-D-glycero-D-gulo-heptitol (21). To a dry flask equipped with a drying tube was added the C-glycoside methyl ether 20 (0.54 g, 1.16 mmol) along with 30% HBr in acetic acid (5 mL, 25 mmol) at 0° C. The mixture was stirred for 30 min and then left at rt for 18 h. The mixture was diluted with methylene chloride and then carefully washed with water and saturated $NaHCO_3$ solution. The organic layer was dried ($MgSO_4$), concentrated, and chromatographed (2:1 then 1:1 hexanes/ethyl acetate) to give 593 mg (97%) of white solid, mp 141-142° C. $[\alpha]_D$ -4.67 (c 2.57, DMK); IR (cm$^{-1}$) 2993 (w), 2952 (w), 1754 (s), 1440 (w), 1374 (m), 1244 (s), 1105 (w), 1052 (m); $^1$H NMR (DMK-$d_6$) δ 1.92-1.98 (m, 12H), 2.72 (dd, 1H, J=7.3, 8.6 Hz), 2.88 (dd, 1H, J=3.2, 7.3 Hz), 3.77-3.85 (m, 2H), 4.00 (dd, 1H, J=2.4, 6.1 Hz), 4.21 (dd, 1H, J=5.9, 6.1 Hz), 4.63 (s, 2H), 4.86 (t, 1H, J=2.6 Hz), 4.97 (t, 1H, J=9.6 Hz), 5.22 (t, 1H, J=9.6 Hz), 7.25 (d, 2H, J=8.2 Hz); 7.37 (d, 2H, J=8.2 Hz); $1^{13}$C NMR (DMK-$d_6$) δ 20.49, 20.60, 34.32, 38.07, 63.03, 69.23, 72.82, 74.85, 76.07, 78.40, 129.72, 130.68, 137.12, 138,92, 169.97, 170.10, 170.30, 170.52; HRMS (ES) calcd for $C_{22}H_{27}BrO_9$ (M+Na) 537.0736, found 537.0724.

flame dried flask under argon atmosphere was added THF (10 mL) along with LiHMDS (1.0 M in hexanes, 0.78 mL, 0.78 mmol) The mixture was cooled to −78° C. upon which the silyl cyanohydrin of retinal 16 (218 mg, 51 mmol) in THF (5 mL) was added by cannulation into the flask. The dark red solution was allowed to stir for 30 min at −78° C. The crystalline glucoside bromide 21 (277 mg, 0.53 mmol) in THF (5 mL) was cannulated into the flask and the mixture stirred for 2 h at −78° C., after which the solution changed to light red. The reaction was taken out of the cold bath and quenched with a solution of 1 M $NH_4Cl$ (1 mL). The mixture was extracted with ethyl acetate (3×) and the organic layers were combined, washed with brine, dried ($Na_2SO_4$), filtered, and concentrated. The crude alkylated product was taken up in 1% aqueous THF (20 mL) and chilled to 0° C. TBAF (134 mg, 0.51 mmol) was added and the darkened solution stirred overnight while warming to rt. The reaction was diluted with water and extracted with ethyl acetate (3×). The organic layers were combined, washed with brine, dried ($Na_2SO_4$), filtered, concentrated, and chromatographed (2:1 hexanes/ethyl acetate) to give 132 mg (36% over two steps) of yellow foam. $^1$H NMR (DMK-$d_6$) δ 1.00 (s, 6H), 1.43-1.46 (m, 2H), 1.58-1.59 (m, 2H), 1.68 (s, 3H), 1.90 (s, 3H), 1.92 (s, 3H), 1.94 (s, 3H), 1.95 (s, 3H), 2.26, (s, 3H), 2.70-2.87 (m, 2H), 3.30 (s, 2H), 3.74-3.83 (m, 2H), 3.97 (d, 1 , J=12.0 Hz), 4.19 (dd, 1H, J=5.9, 12.0 Hz) 4.85 (t, 1H, J=9.6 Hz), 4.95 (t, 1H, J=9.6 Hz), 5.20 (t, 1H,

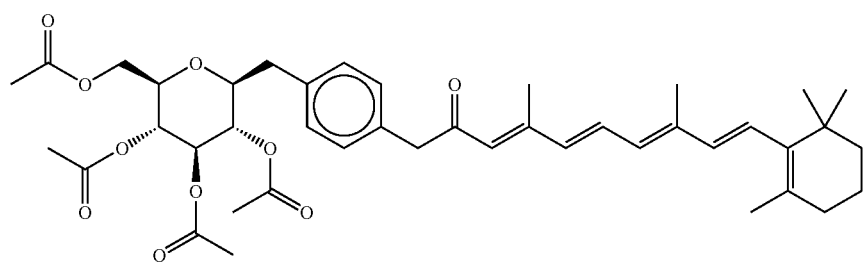

22

2,6-Anhydro-7-deoxy-7-[4-(retinoylmethyl)-phenyl]-3,4,5,7-tetra-O-acetyl-D-glycero-D-gulo-heptinol (22). To a J=9.6 Hz), 6.15-6.37 (m, 5H), 7.10-7.17 (m, 5H); HRMS (ES) calcd for $C_{42}H_{54}O_{10}$ (M+Na) 741.3615, found 741.3617.

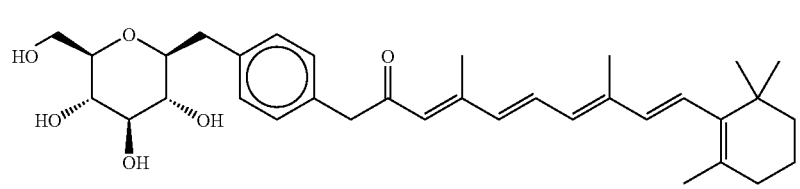

23

2,6-Anhydro-7-deoxy-7-[4-(retinoylmethyl)-phenyl]-D-glycero-D-gulo-heptinol (23). To a flask was added the protected glucoside-retinoid conjugate 22 (130 mg, 0.18 mmol) dissolved in methanol (75 mL) and chilled to 4° C. Potassium carbonate (25 mg, 0 18 mmol) was added and allowed to stir for 20 h. The reaction was then cooled to 0° C. and carefully adjusted to pH 5 with 1 N HCl. The solution was extracted with ethyl acetate and the organic layers were combined, dried ($Na_2SO_4$), and carefully concentrated. The residue was chromatographed on reverse-phase silica gel (gradient 70:30 to 85:15 methanol/water) to yield 49 mg (49%) of yellow foam. UV $\lambda_{max}$=380 nm ($\epsilon$=34567); HPLC $t_R$=13.8 min (1 mL/min, 85:15 MeOH:$H_2O$ both with 10 mM $NH_4OAc$); IR ($cm^{-1}$) 3388 (br), 2948 (m), 2846 (m), 1652 (m), 1554 (w), 1456 (w), 1415 (w), 1113 (w), 1056 (m), 1016 (s), 694 (br); $^1H$ NMR(DMK-$d_6$) δ 1.02 (s, 6H), 1.45-1.48 (m, 2H), 1.58-1.64 (m, 2H), 1.69 (s), 3H), 2 01 (s, 3H), 2.03-2.05 (m, 2H), 2.29, (s, 3H), 2.65 dd, 1H, J=8.3, 14.3 Hz), 3.09-3.38 (m, 6H), 3.57-3.60 (m, 1H), 3.70 (s, 3H), 6.15-6.35 (m, 5H), 7.12-7.26 (m, 5H); $^{13}C$ NMR (DMK-$d_6$) δ 13.43, 14.66, 20.41, 22.46, 26.31, 30.95, 34.14, 38.69, 40.85, 52.34, 63.81, 72.70, 75.05, 80.37, 81.31, 81.50, 129.82, 130.43, 130.90, 131.20, 131.48, 133.64, 134.46, 137.31, 138.96, 139.08, 140.89, 152.57, 198 97; HRMS (ES) calcd for $C_{34}H_{46}O_6$ (M+Na) 573.3192, found 573.3204.

Biological:

Animal Studies: Mammary tumors were induced by intragastric intubation of 50-day old female Sprague-Dawley rats (Harlan Industries, Indianapolis, Ind.) with a single dose of 15 mg DMBA in 1.0 ml of sesame oil per rat. The rats were then maintained on a powdered Teklad 22/5 rodent chow diet (W) 8640 (Harlan Industries, Indianapolis, Ind.), and allowed food and water ad libitum. Four months later, rats which had developed palpable tumors were randomly assigned to the experimental groups (4 rats/group). The retinoid-treated groups were fed diets supplemented with 2 mmol/kg diet of atRA, 4-HPR, or 4-HBRCG, respectively. The retinoids were added to the diet in a vehicle consisting of 25 ml of ethanol: tricaprylin (1:4 v/v) plus 2% (w/v) of α-tocopherol as previously described.[9] This vehicle was also added to the control diet. The additives were blended into the chow diets using a Hobart food mixer. The diets were fed in stainless steel feeders designed with food hoppers. The food was replaced weekly with freshly prepared diets. Food consumption was determined once weekly, and from that the average daily consumption/rat was estimated. These diets were continuously fed for 22 days. Animals were also weighted weekly and monitored for general health status and signs of possible toxicity due to treatment.

Baseline measurement of initial tumor sizes, numbers and rat body weights were determined immediately before commencement of treatments, and final measurements were recorded just prior to sacrifice of the animals. Animals were palpated for tumors twice weekly and tumor diameters were measured weekly by a micrometer caliper. Tumor volumes were calculated using the formula [$V=4/3\pi r^3$] where r is one-half the mean of the sum of the largest diameter and the axis at right angle to it. All tumors as well as lungs, liver, kidney and femur were excised at the end of the experiment for chemical and histopathological evaluation. Blood samples were also taken from each animal for determination of plasma retinol and triglyceride levels.

Plasma Triglyceride Measurement. Bloods were drawn from anesthetized animals in the presence of EDTA as an anticoagulant, and the resulting plasma was used for the measurement of plasma "true" triglyceride levels using a kit from Sigma-Aldrich (Saint Louis, Mo.). Briefly, the total plasma triglyceride and glycerol concentrations were determined, and the glycerol component was subtracted from the total plasma triglyceride measurement to obtain the "true" serum triglyceride concentration.

Plasma Retinoid Assay. To 500 μL of plasma was added 150 μL of ethanol containing 0.75 μg of internal standard (N-(4-chlorophenyl) retinamide). After mixing 30 sec., 500 μL of ethyl acetate was added followed by 1 min. of mixing and centrifugation for 5 minutes at 1000 rpm in an IEC CL centrifuge. The ethyl acetate layer was removed and syringe filtered through a 0.45 um filter. The ethyl acetate extraction was repeated two more times. The combined extracts were evaporated and the residue reconstituted in 100 μL of methanol. The methanol extract (20 μL) was analyzed by HPLC on a Beckman Instruments model 127 instrument equipped with a model 166 UV detector. Chromatography was done on a precolumn equipped 250×4.6 mm Bechman Ultrasphere ODS column with an 85% methanol/water mobile phase (both containing 10 mM ammonium acetate) flowing at 1 mL/min. Analysis for both internal standard and retinol was conducted at 350 nm and internal standard recoveries and retinol levels were determined by comparison with standard curves, with adjustment of the retinol level based on recovery. Recoveries of internal standard averaged ca. 78%. Previous extraction of plasma from vitamin A deficient rats showed no substances interfering with the elution position of the retinol or internal standard. In the 4-HPR treated group, plasma levels of this retinoid were evaluated simultaneously in the same samples as above. In order to avoid interfering substances, plasma treatment retinoid levels for RA and 4-HBRCG were measured using the above system and a step gradient of 75% methanol for 15 min. followed by 85% methanol for 40 minutes.

Bone Mineral Content. The femur was disarticulated from the leg, and the adhering soft tissue was removed by dissection. Femurs were scanned using the Lunar PIXImus 2 system (Model X2608, General Electric using the LUNAR software version 1.45), and control measurements were made using the small animal quality control phantom. Femurs were scanned 5 times each with re-positioning at each measure. The average value of the bone mineral content (BMC) in grams for each animal is reported as one independent measure.

Nuclear Retinoid Receptor Binding Assay. Competition of 3 and 7 and 4-HBRCGlucose with [$^3H$]-all-trans-RA (4.2-4.6 nM) for binding to RARβ and RARγ and with [$^3H$]-9-cis RA (1.9 nM) for binding to RXRγ was determined using an in vitro ligand binding assay.[41,42] [$^3H$]-all-trans-RA (40.5 Ci/mmole) or [$^3H$]-9-cis-RA (69.4 Ci/mmole) was added to receptor-containing extracts in the absence and presence of increasing concentrations of competing ligands at 4° C. for 3 hr. A hydroxylapatite (HAP) assay was used to separate ligand bound to receptor from that free in solution, and the radioactivity associated with the HAP pellet was measured by scintillation counting. Isolation of RNA and quantitative PCR. Total and polyA$^+$RNA was isolated as described.[43] Briefly, lung and liver tissue was collected and flash-frozen in liquid nitrogen until use. Tissue (0.5 to 1 g) was homogenized in buffer (1:10; wt/vol), and total RNA was isolated according to the method of Chomeczynski and Sacchi.[44]

A rat CYP26A1 partial cDNA was generated by PCR amplification from E10.5 day rat embryo cDNA. The upstream (5' GCA GAT GAA GCG CAG GAA ATA CG 3') (SEQ. ID. NO: 1) and downstream (5' CCC ACG AGT GCT CAA TCA GGA 3') (SEQ. ID. NO: 2) primers were designed based on the murine cDNA (gi:6681100). The 635 bp cDNA was subcloned into pGEM-Teasy (Promega, Madison, Wis.)

and sequenced. Similarly, a rat CYP26B1 partial cDNA was generated by PCR amplification from E11.5 day rat embryo cDNA. The upstream (5' GCT ACA GGG TTC CGG CTT CCA GTC 3') (SEQ. ID. NO: 3) and downstream (5' TCC AGG GCG TCC GAG TAG TCT TTG 3') (SEQ. ID. NO: 4) primers were designed based on the murine cDNA (gi: 31341987), and the 606 bp control cDNA was subcloned and sequenced.

The quantitative polymerase chain reaction (Q-PCR) assay was performed using the real-time LightCycler system (Roche, Indianapolis, Ind., USA) with LightCycler faststart DNA master SYBR green1 kit (Roche, Indianapolis Ind.) according to the manufacturer's protocols. Poly(A)$^+$RNA (0.5 to 1 µg) was reverse transcribed (RT) using AMV enzyme (Promega, Madison, Wis.) and random hexamers. The following primer sets were used for Q-PCR: CYP26A1, upstream 5'-ATG ATT CCT CGC ACA AGC AG-3' (SEQ. ID. NO: 5), downstream 5'-GCT CCA GAC AAC CGC TCA CT-3' (SEQ. ID. NO: 6); CYP26B1, upstream 5'-AGG CCC AGC GAC TTA CCT TC-3' (SEQ. ID. NO: 7), downstream 5'-AGG GCG TCC GAG TAG TCT TT-3' (SEQ. ID. NO: 8); and GAPDH, upstream 5'-TGA AGG TCG GTG TGA ACG GAT TTG GC-3' (SEQ. ID. NO: 9), downstream 5'-CAT GTA GGC CAT GAG GTC CAC CAC-3' (SEQ. ID. NO: 10). The primer sets for CYP26A1, CYP26B1 and GAPDH amplify 409 bp to 519 bp (gi:18426827), 708 bp to 957 bp (gi: 31220748), and 854 bp to 1836 bp (gi:31377487), respectively.

Growth inhibition of MCF-7 human breast cancer cells. MCF-7 cells were obtained from the American Type Culture Collection, Manassas, Va. They were maintained in DMEM medium supplemented with 4 g/L glucose, 3.7 g/L sodium bicarbonate and 10% heat-inactivated fetal calf serum. Cells were passaged into 12-well plates, cultured for 24 hours, after which time they were dosed with vehicle (0.2% ethanol) or retinoids; medium was changed and fresh vehicle or retinoids were added daily. Cells were harvested and the number of live cells was assessed using fluorescein diacetate, which yields a fluorescent product upon cleavage by metabolically active cells. Using fluorescent microscopy, at least 200 cells/well were counted with a hemacytometer.

Statistical analysis. Descriptive statistics on tumor volumes, tumor numbers, retinol, triglyceride levels and BMC were examined and compared among the experimental groups. The statistical significance of the groups' comparisons was obtained using analysis of variance (ANOVA), ANOVA with repeated measures, and non-parametric tests. Values were considered significant when the $p \leq 0.05$.

REFERENCES

1. Moon, R. C.; Metha, R. G.; Rao, K. V. N. Retinoids and cancer in experimental animals. In *The Retinoids: Biology, Chemistry, and Medicine,* 2nd *Edition;* Sporn, M. B., Roberts, A. B., Goodman, D. S., Eds.; Raven Press: New York, 1994; p 573.
2. Veronesi, U.; De Palo, G.; Marubini, E.; Costa, A.; Formelli, F.; Mariani, L.; Decensi, A.; Camerini, T.; Rosselli Del Turco, M.; Di Mauro, M. G.; Muraca, M. G.; Del Vecchio, M.; Pinto, C.; D'Aiuto, G.; Boni, C.; Campa, T.; Magni, A.; Miceli, R.; Perloff, M.; Malone, W. F.; Sporn, M. B. *J Natl. Cancer Inst.* 1999, 91, 1847.
3. Formelli, F.; Carsana, R.; Costa, A.; Buranelli, F.; Campa, T.; Dossena, G.; Magni, A.; Pizzichetta, M. *Cancer Res.* 1989, 49, 6149.
4. Formelli, F.; Clerici, M.; Campa, T.; Gaetana Di Mauro, M.; Magni, A.; Mascotti, G.; Moglia, D.; De Palo, G.; Costa, A.; Veronesi, U. *J Clin. Oncol.* 1993, 11, 2036.
5. Camerini, T., Mariani, L.; De Palo, G.; Marubini, E.; Gaetana Di Mauro, M.; Decensi, A.; Costa, A.; Veronesi, U. *J. Clin Oncol.* 2001, 19, 1664.
6. Mulder, G. J.; Coughtrie, M. W. H.; Burchell, B. In *Conjugation Reactions in Drug Metabolism: An Integrated Approach;* Mulder, G. J., Ed.; Taylor and Francis: London, 1990; p 52.
7. Abou-Issa, H.; Curley, R. W., Jr.; Panigot, M. J.; Tanagho, S. N.; Sidhu, B. S.; Alshafie, G. A. *Anticancer Res.* 1997, 17, 3335.
8. Panigot, M. J.; Humphries, K. A.; Curley, R. W., Jr. *J. Carbohydr. Chem.* 1994, 13, 303.
9. Abou-Issa, H. M.; Alshafie, G. A.; Curley, R. W., Jr.; Wong, M. F.; Clagett-Dame, M.; Repa, J. J.; Sikri, V. *Anticancer Res.* 1999, 19, 999.
10. Walker, J. R.; Alshafie, G.; Abou-Issa, H.; Curley, R. W., Jr. *Bioorg. Med. Chem. Lett.* 2002, 12, 2447.
11. Wu, J. M.; DiPietrantonio, A. M.; Hsieh, T.-C. *Apoptosis* 2001, 6, 377.
12. Weiss, K. L.; Alshafie, G.; Chapman, J. S.; Mershon, S. M.; Abou-Issa, H.; Clagett-Dame, M.; Curley, R. W., Jr. *Bioorg. Med. Chem. Lett.* 2001, 11, 1583.
13. Chapman, J. S.; Weiss, K. L.; Curley, R. W., Jr.; Highland, M. A.; Clagett-Dame, M. *Arch. Biochem. Biophys.* 2003, 419, 234.
14. Johns, B. A.; Pan, Y. T.; Elbein, A. D.; Johnson, C. R. *J. Am. Chem. Soc.* 1997, 119, 4856.
15. Johnson, C. R.; Johns, B. A. *Synlett* 1997, 1406.
16. Petasis, N. A.; Bzowej, E. I. *J. Am. Chem. Soc.* 1990, 112, 6392.
17. Csuk, R.; Glaenzer, B. I. *Tetrahedron* 1991, 47, 1655.
18. RajanBabu, T. V.; Reddy, G. S. *J. Org. Chem.* 1986, 51, 5458.
19. Wong, M. F.; Weiss, K. L.; Curley, R. W., Jr. *J. Carbohydr. Chem.* 1996, 15, 763.
20. Davis, N. J.; Flitsch, S. L. *Tetrahedron Lett.* 1993, 34, 1181.
21. Robarge, M. J. Stable analogues of retinoid-O-glucuronides: Synthesis and biological activity. Dissertation, The Ohio State University, 1996.
22. Kelley, J. L.; Baker, B. R. *J. Med. Chem.* 1982, 25, 600.
23. Katz, H. E. *J. Org. Chem.* 1985, 50, 2086.
24. Stork, G.; Maldonado, L. J. *Am. Chem. Soc.* 1971, 93, 5286.
25. Kobayashi, S.; Tsuchiya, Y.; Mukaiyama, T. *Chem. Lett.* 1991, 4, 537.
26. Weiss, K. L. Structural probes of retinoid action. Dissertation, The Ohio State University, 2001.
27. Loerch, J. D.; Underwood, B. A.; Lewis, K. C. *J. Nutr.* 1979, 109, 778.
28. Costa, A.; Malone, W.; Perloff, M.; Buranelli, F.; Campa, T.; Dossena, G.; Magni, A.; Pizzichetta, M.; Andreoli, C.; Del Vecchio, M.; Formelli, F.; Barbieri, A. *Eur. J. Clin. Oncol.* 1989, 25, 805.
29. Zanotti, G.; Berni, R. *Vitam. Horm.* 2004, 69, 271.
30. Gerber, L. E.; Erdman, J. W. Jr. *J. Nutr.* 1979, 109, 580.
31. Gerber, L. E.; Erdman, J. W. Jr. *J. Nutr.* 1980, 110, 343.
32. Standevan, A. M.; Beard, R. L.; Johnson, A. T.; Boehm, M. F.; Escobar, M.; Heyman, R. A.; Chandraratna, R. A. *Fund. Appl. Toxicol.* 1996, 33, 264.
33. Dhem, A.; Goret-Nicaise, M. *Food Chem. Toxic.* 1984, 22, 199.
34. DiGiovanna, J. J. *J. Am. Acad. Dermatol.* 2001, 45, S176.
35. Rohde, C. M.; DeLuca, H. *J. Nutr.* 2004, 133, 777.

36. Decensi, A.; Torrisi, R.; Gozza, A.; Severi, G.; Bertelli, G.; Fontana, V.; Pensa, F.; Carozzo, L.; Traverso, A.; Milone, S.; Dini, D.; Costa, A. *Breast Cancer Res. Treat.* 1999, 53, 145.
37. Curley, R. W., Jr; Abou-Issa, H.; Panigot, M. J.; Repa, J. J.; Clagett-Dame, M.; Alshafie, G. *Anticancer Res.* 1996, 16, 757.
38. White, J. A.; Guo, Y. D.; Baetz, K.; Beckett-Jones, B.; Bonasoro, J.; Hsu, K. E.; Dilworth, F. J.; Jones, G.; Petkovich, M. *J. Biol. Chem.* 1996, 271, 19922.
39. Loudig, I.; Babichuk, C.; White, J.; Abu-Abed, S.; Mueller, C.; Petkovich, M. *Mol. Endocrinol.* 2000, 14, 1483.
40. Modiano, M. R.; Dalton, W. S.; Lippman, S. M.; Joffe, L.; Booth, A. R.; Meyskens, F. L. Jr. *Invest. New Drugs* 1990, 8, 317.
41. Clagett-Dame, M.; Repa, J. J. *Meth. Enzymol.* 1997, 282, 13.
42. Abou-Issa, H.; Curley, R. W., Jr.; Alshafie, G. A.; Weiss, K. L.; Clagett-Dame, M.; Chapman, J. S.; Mershon, S. M. *Anticancer Res.* 2001, 21, 3839.
43. Merrill, R. A.; Plum, L. A.; Kaiser, M. E.; Clagett-Dame, M. *Proc. Natl. Acad. Sci. USA* 2002, 99, 3422.
44. Chomczynski, P.; Sacchi, N. *Anal. Biochem.* 1987, 162, 156.
45. Curley, R. W.; Carson, D. L, Drug Des. Delivery. 1987, 1, 219-224

---

What is claimed is:

1. A compound of Formula I:

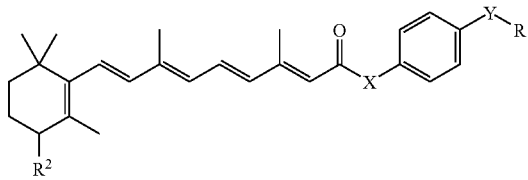

Formula I wherein X is $CH_2$; Y is $C_1$-$C_6$ alkylene; and R is selected from the group consisting of hydrogen, $C_1$-$C_6$ alkyl,

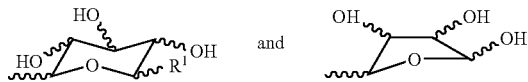  and wherein $R^1$ is selected from the group consisting of H, OH, COOH, $C_1$-$C_6$ alkyl, alkenyl, alkynyl, and $C_1$-$C_6$-hydroxyalkyl; $R^2$ is OH;
or a salt thereof.

2. The compound of claim 1, wherein R is hydrogen.
3. The compound of claim 1, wherein R is $C_1$-$C_6$ alkyl.
4. The compound of claim 1, wherein R is

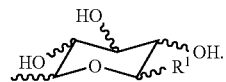

5. The compound of claim 4, wherein $R^1$ is H.
6. The compound of claim 4, wherein $R^1$ is COOH.
7. The compound of claim 4, wherein $R^1$ is $CH_2OH$.
8. The compound of claim 4, wherein $R^1$ is OH.
9. The compound of claim 1, wherein R is

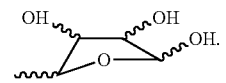

10. A pharmaceutical composition for inhibiting formation of breast cancer and treating breast cancer in mammals, the composition comprising an effective breast cancer cell growth-inhibiting amount of a compound according to claim 1, or a pharmaceutically-suitable salt thereof, optionally in combination with a pharmaceutically-suitable carrier.

11. A method of inhibiting formation of breast cancer and treating breast cancer in mammals, the method comprising administering a breast cancer cell growth-inhibiting amount of a compound according to claim 1, or a pharmaceutically-suitable salt thereof, to a patient in need thereof.

* * * * *

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial
<220> FEATURE:
<223> OTHER INFORMATION: PCR primer

<400> SEQUENCE: 1
gcagatgaag cgcaggaaat acg                                            23

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
cccacgagtg ctcaatcagg a                                              21

<210> SEQ ID NO 3
<211> LENGTH: 24
<212> TYPE: DNA
<213> ORGANISM: Artificial
<220> FEATURE:
<223> OTHER INFORMATION: PCR primer

<400> SEQUENCE: 3
gctacagggt tccggcttcc agtc                                           24

<210> SEQ ID NO 4
<211> LENGTH: 24
<212> TYPE: DNA
<213> ORGANISM: Artificial
<220> FEATURE:
<223> OTHER INFORMATION: PCR primer

<400> SEQUENCE: 4
tccagggcgt ccgagtagtc tttg                                           24

<210> SEQ ID NO 5
<211> LENGTH: 20
<212> TYPE: DNA
<213> ORGANISM: Artificial
<220> FEATURE:
<223> OTHER INFORMATION: PCR primer
```

-continued

```
<400> SEQUENCE: 5
atgattcctc gcacaagcag                                                    20

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
gctccagaca accgctcact                                                    20

<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
aggcccagcg acttaccttc                                                    20

<210> SEQ ID NO 8
<211> LENGTH: 20
<212> TYPE: DNA
<213> ORGANISM: Artificial
<220> FEATURE:
<223> OTHER INFORMATION: PCR primer

<400> SEQUENCE: 8
agggcgtccg agtagtcttt                                                    20

<210> SEQ ID NO 9
<211> LENGTH: 26
<212> TYPE: DNA
<213> ORGANISM: Artificial
<220> FEATURE:
<223> OTHER INFORMATION: PCR primer

<400> SEQUENCE: 9
tgaaggtcgg tgtgaacgga tttggc                                             26

<210> SEQ ID NO 10
<211> LENGTH: 24
<212> TYPE: DNA
<213> ORGANISM: Artificial
<220> FEATURE:
<223> OTHER INFORMATION: PCR primer

<400> SEQUENCE: 10
catgtaggcc atgaggtcca ccac                                               24
```